United States Patent
Seki et al.

(10) Patent No.: US 7,838,229 B2
(45) Date of Patent: Nov. 23, 2010

(54) IDENTIFICATION MARKER RESPONSIVE TO INTERFERON THERAPY FOR RENAL CELL CANCER

(75) Inventors: Toyokazu Seki, Tokushima (JP); Takayuki Shiratsuchi, Tokushima (JP); Osamu Ogawa, Kyoto (JP); Seiji Naito, Fukuoka (JP); Taiji Tsukamoto, Sapporo (JP); Hiroshi Toma, Shinjuku-ku (JP); Yoshihiko Hirao, Kashihara (JP); Susumu Kagawa, Tokushima (JP); Yoshiaki Nose, Fukuoka (JP); Tsuyoshi Nakamura, Nagasaki (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 512 days.

(21) Appl. No.: 11/666,056

(22) PCT Filed: Oct. 24, 2005

(86) PCT No.: PCT/JP2005/019491

§ 371 (c)(1),
(2), (4) Date: Apr. 23, 2007

(87) PCT Pub. No.: WO2006/046505

PCT Pub. Date: May 4, 2006

(65) Prior Publication Data

US 2008/0199859 A1    Aug. 21, 2008

(30) Foreign Application Priority Data

Oct. 28, 2004 (JP) .............................. 2004-314160

(51) Int. Cl.
*C07H 21/04* (2006.01)
*C12Q 1/68* (2006.01)

(52) U.S. Cl. ................... 435/6; 435/91.1; 435/91.2; 536/23.1; 536/24.3

(58) Field of Classification Search ............. None
See application file for complete search history.

(56) References Cited

U.S. PATENT DOCUMENTS

2003/0096237 A1   5/2003  Certa

2004/0043379 A1   3/2004  Hashimoto et al.

FOREIGN PATENT DOCUMENTS

| JP | 2001-136973 A | 5/2001 |
| JP | 2003-088382 A | 3/2003 |
| JP | 2003-339380 A | 12/2003 |
| JP | 2004-507253 A | 5/2004 |
| WO | 2004033650 A2 | 4/2004 |

OTHER PUBLICATIONS

Shen et al. (BMC Cell Biology, vol. 3, 2002).*
Hirschhorn et al. (Genetics in Medicine. vol. 4, No. 2, pp. 45-61, Mar. 2002).*
Lucentini (The Scientist; 2004, vol. 24, p. 20.*
Ioannidis (Nature Genetics, vol. 29, pp. 306-309, Nov. 2001).*
Supplementary European Search Report in International Application No. PCT/JP2005/019491 dated Jun. 16, 2009.
Schlaak, J. F. et al., "Cell-type and donor specific transcriptional responses to interferon-alpha. Use of customized gene arrays", J. Biol. Chem., 277 (51), p. 49428-37. Dec. 20, 2002.
Franzke, A. et al., "HLA phenotype an cytokine-induced tumor control in advanced renal cell cancer", Cancer Biother Radiopharm, 16(5) p. 401-9, Oct. 2001.
Basturk, B. et al., "Cytokine gene polymorphisis as potential risk and protective factors in renal cell carcinoma", Cytokine, 30(1), p. 41-5, Apr. 7, 2005.
Brookes, A. J. "The essence of SNPs", Gene, 234, p. 177-186, 1999.
Cargill, M. et al., "Characterization of single-nucleotide polymorphisis in coding regions of human genes", Nature Genet., 22, p. 231-238, 1999.
Evans, W. E. & Relling, M. V., "Pharmacogenomics: functional genomic into rational therapeutics", Science, 286, P487-491, 1999.
Chinese Office Action issued Aug. 21, 2009, in CN 200580037257.3.
Genbank Accession No. ss14282437, published Nov. 5, 2003, retrieved from http://www.ncbi.nim.nih.gov/projects/SNP/snp_retrieve.cgi?subsnp_id=14282437.

* cited by examiner

*Primary Examiner*—Jeanine A Goldberg
(74) *Attorney, Agent, or Firm*—Sughrue Mion, PLLC

(57) ABSTRACT

The present invention provides an identification marker responsive to IFN therapy for renal cell cancer and a means of detecting the same. Namely, a method which comprises preparing a genomic DNA of a human gene or a complementary strand thereof from a specimen of a patient with renal cell cancer, analyzing the DNA sequence of the genomic DNA or the complementary strand thereof to determine the gene polymorphism of the human gene, and evaluating the tumor-suppression effect of IFN therapy on renal cell cancer by using the polymorphism as an indicator.

8 Claims, No Drawings

IDENTIFICATION MARKER RESPONSIVE TO INTERFERON THERAPY FOR RENAL CELL CANCER

CROSS REFERENCE TO RELATED APPLICATIONS

This application is a National Stage of International Application No. PCT/JP2005/019491 filed on Oct. 24, 2005, claiming priority based on Japanese Patent Application No. 2004-314160, filed Oct. 28, 2004, the contents of all of which are incorporated herein by reference in their entirety.

TECHNICAL FIELD

The present invention relates to a method for evaluating a tumor-suppression effect of interferon administration (treatment response) on renal cell cancers using human gene polymorphism as an indication (marker), an oligonucleotide used in such a method, and a detection kit for such a gene polymorphism.

BACKGROUND ART

Renal cell cancer is an intractable disease with low response rates to any of the therapies presently practiced, such as pharmacotherapy using chemotherapeutic drugs, immunotherapeutic drugs, etc., radiotherapy, surgical operation, and/or the like. Further, by the time renal cell cancer is identified, cases that have already developed distant metastasis are reportedly as high as about 30%. Excluding surgical operation, immunotherapy using interferons (IFNs) among the above pharmacotherapies, is particularly considered most effective; however, response rates attained by such a therapy are as low as only about 15% when IFN-α is administered singly, and 10 to 15% when IFN-γ is administered singly. Even when used in combination with anti-cancer agents, there is no other therapy that provides higher effect than that of the IFN-α monotherapy. The currently practiced immunotherapy using IFN is primarily a long-term maintenance therapy with single use of IFN-α, or combined use with IFN-γ.

Meanwhile, progress of genome sciences are rapidly elucidating pharmacokinetics, and gene polymorphisms of enzymes, proteins, etc., which are relevant to drug responsibility. In human genome analysis, single nucleotide polymorphisms (SNPs) have been receiving attention since gene polymorphism markers are found most frequently. Such SNPs are known to have been useful for analyzing human genome relevant to common diseases, drug responses, etc. (see non-patent documents 1, 2 and 3). Haplotype analysis using a plurality of SNPs is also known to have been useful for analyzing the susceptibility to diseases (see non-patent document 4).

Lately, to establish so-called order-made medicine for individual patients, studies to reveal a relationship between a given gene polymorphism and drug sensitivity/drug responsibility of a patient have been proposed.

A known method for predicting the effects of IFN therapy analyzes the relationship of MxA-8/MxA123 MBL-221/MBL-CLDcodon54 SNPs on the genome of an HCV (human hepatitis C virus (human HCV))-infected patient with IFN-α responders (patients responsive to the therapy) and non-responders (patients not responsive to the therapy), thereby predicting and evaluating the degree of IFN treatment response of the HCV-infected patient (patent document 1). Another known method predicts IFN treatment response using SNP in the promoter region and at position 134 of IFN-α receptor 2 gene, as gene polymorphism markers (patent document 2). This document discloses target diseases selected from the group consisting of hepatitis B, hepatitis C, glioblastoma, medulloblastoma, astrocytoma, skin malignant melanoma, and like hepatitis, renal cancers, multiple myeloma, hairy cell leukemia, chronic myelogenous leukemia, subacute sclerosing panencephalitis, virus encephalitis, systemic zoster and varicella of a patient with immunosuppression, epipharynx anaplastic carcinoma, viral internal ear infectious disease accompanied by hypacusis, herpetic keratitis, flat condyloma, condyloma acuminatum, conjunctivitis caused by adenovirus and/or herpesvirus infection, genital herpes, cold sore, uterine cervix carcinoma, cancerous hydrothorax, keratoacanthoma, basal cell carcinoma, and chronic active hepatitis δ.

Further, to evaluate response of IFN-α therapy for hepatitis C, an also known method is to measure substitution from guanine (G) to adenine (A) at position 196 in the promoter region of IRF-1 gene (see patent document 3).

To date, however, there has been no document specifically reporting a relationship between IFN therapy response to renal cell cancers and given SNPs.

For IFN-α responders and non-responders, there have already been several hundred gene expression profiles reported (see non-patent document 4 and patent document 4). These profiles were created using technologies such as DNA chips (high density oligonucleotides or microarrays), differential display, differential cDNA arrays, SAGE (serial analysis of gene expression), expressed sequence tag database comparison, or the like. These methods were used to analyze gene expression in colon, breast, ovarian carcinomas, multiple sclerosis lesions, leukemia, and renal cell carcinomas. Non-patent document 4 further includes genes such as IRF2, STAT1, STAT2, STAT4, STAT5, STAT6, etc.; however, no SNPs of specific genes used in the present invention are disclosed.

[Patent document 1] Unexamined Japanese Patent Publication No. 2003-88382
[Patent document 2] Unexamined Japanese Patent Publication No. 2003-339380
[Patent document 3] Unexamined Japanese Patent Publication No. 2001-136973
[Patent document 4] Unexamined Japanese Patent Publication No. 2004-507253
[Non-patent document 1] Brookes, A. J., "*The essence of SNPs*", Gene, USA, (1999), 234, 177-186
[Non-patent document 2] Cargill, M, et al., "*Characterization of single-nucleotide polymorphisms in coding regions of human genes*", Nature Genet., USA, (1999), 22, 231-238
[Non-patent document 3] Evans, W. E., & Relling, M. V., "*Pharmacogenomics: translating functional genomics into rational therapeutics*", Science, USA, (1999), 286, 487-491
[Non-patent document 4] Schlaak, J. F., et. al., "*Cell-type and Donor-specific Transcriptional Responses to Interferon-α*", J. Biol. Chem., (2002) 277, 51, 49428-49437

DISCLOSURE OF THE INVENTION

Problems to be Solved by the Invention

A primary object of the present invention is to provide a means of evaluating therapeutic response of interferon administration to renal cell cancers (tumor-suppression effect).

Means for Solving the Problems

To solve the aforementioned problems, the present inventors arbitrarily selected 33 genes as gene polymorphism analysis candidates, which included IFN-related genes, genes reportedly relevant to IFN-γ signal transduction, and genes that reportedly showed gene expression changes by IFN addition/administration. The inventors searched for SNPs on these candidate genes using public polymorphism databases, and selected 463 candidate SNPs. Then, frequency difference of these selected SNPs was determined using as genomic DNA samples derived from two patient groups: IFN responder group with tumor-suppression effect in renal cell cancers by IFN-α administration (patients responded to the therapy), and IFN non-responder group (patients who did not respond to the therapy). As a result, the inventors have found that SNPs showing statistical meaningful differences between the above two groups are present on the following 8 genes.

(1) STAT3 gene (Signal transducer and activator of transcription 3: STAT3 (GenBank Accession No. NT_010755)) (hereinafter referred to as "STAT3 gene"), (2) SSI3 gene (Suppressor of cytokine signaling 3: SSI3 (GenBank Accession No. NT_010641)) (hereinafter referred to as "SSI3 gene"), (3) IL-4R gene (Interleukin 4 receptor (GenBank Accession No. NT_010393)) (hereinafter referred to as "IL-4R gene"), (4) IRF2 gene (Interferon regulatory factor 2: IRF2 (GenBank Accession No. NT_022792)) (hereinafter referred to as "IRF2 gene"), (5) ICSBP gene (Interferon consensus sequence-binding protein 1: ICSBP1 (GenBank Accession No. NT_019609) (hereinafter referred to as "ICSBP1 gene"), (6) PTGS1 gene (Prostaglandin-endoperoxide synthase 1: PTGS1 (GenBank Accession No. NT_008470) (hereinafter referred to as "PTGS1 gene"), (7) PTGS2 gene (Prostaglandin-endoperoxide synthase 2: PTGS2) (GenBank Accession No. NT_004487) (hereinafter referred to as "PTGS2 gene"), and (8) TAP2 gene (Transporter, ATP-binding cassette, Major histocompatibility complex 2: TAP2) (GenBank Accession No. NT_007592) (hereinafter referred to as "TAP2 gene").

The inventors have extended further research about the relationship between SNPs present on the above genes and IFN therapy response to renal cell cancers. Consequently, the inventors have confirmed 16 SNPs which are strongly relevant to tumor-suppression effects of IFN-α administration for renal cell cancers, and realized that these SNPs can be used as markers to evaluate tumor suppression effects after IFN therapies. More specifically, the inventors have found that the detection of these SNPs enables the prediction of tumor-suppression effects of IFN administration (treatment response) for renal cell cancers (predictive diagnosis). Based on these findings, the present invention has been accomplished as a result of further studies.

The present invention provides a method for evaluating tumor-suppression effects after IFN therapy on a patient with renal cell cancer as described in articles 1 to 11 below.

Article 1. A method for evaluating tumor suppression by IFN therapy on a patient with renal cell cancer, the method comprising steps (i) to (iv) below;

(i) a step of obtaining a gene sample (genomic DNA sample) derived from a patient with renal cell cancer, (ii) a step of preparing a genomic DNA or a complimentary chain thereof of at least one gene selected from the group consisting of STAT3 gene, SSI3 gene, IL-4R gene, IRF2 gene, ICSBP gene, PTGS1 gene, PTGS2 gene, and TAP2 gene, using the gene sample obtained in step (i) above, (iii) a step of analyzing DNA sequence of the genomic DNA or the complimentary chain thereof, and determining gene polymorphism thereof, and (iv) a step of evaluating tumor suppression by IFN therapy on a patient with renal cell cancer, using as a marker at least one gene polymorphism determined in step (iii) above.

Article 2. A method for evaluating tumor suppression by IFN therapy on a patient with renal cell cancer according to Article 1, wherein the gene polymorphism is a polymorphism of at least one gene selected from the group consisting of STAT3 gene, IL-4R gene, IRF2 gene, and TAP2 gene.

Article 3. A method for evaluating tumor suppression by IFN therapy on a patient with renal cell cancer according to Article 1, wherein the gene polymorphism is at least one selected from the group consisting of (a) to (p) below:

(a) gene polymorphism (STAT3-2) with genotype C/T or T/T at position 4243095 of STAT3 gene, and represented by Reference SNP ID number:rs1905341, (b) gene polymorphism (STAT3-3) with genotype C/C at position 4264926 of STAT3 gene, and represented by Reference SNP ID number:rs4796793, (c) gene polymorphism (STAT3-17) with genotype G/G at position 4204027 of STAT3 gene, and represented by Reference SNP ID number:rs2293152, (d) gene polymorphism (STAT3-18) with genotype C/T at position 4050541 of STAT3(KCNH4) gene, and represented by Reference SNP ID number:rs2293153, (e) gene polymorphism (SSI3-1) with genotype A/C at position 10246541 of SSI3 gene, and represented by Reference SNP ID number:rs2280148, (f) gene polymorphism (IL-4R-22) with genotype A/A at position 18686025 of IL-4R gene, and represented by Reference SNP ID number:rs1805011, (g) gene polymorphism (IRF2-67) with genotype A/A at position 17736877 of IRF2 gene, and represented by Reference SNP ID number:rs2797507, (h) gene polymorphism (IRF2-82) with genotype C/C at position 17744613 of IRF2 gene, and represented by Reference SNP ID number:rs796988, (i) gene polymorphism (ICSBP-38) with genotype A/A or A/C at position 390141 of ICSBP gene, and represented by Reference SNP ID number: rs2292982, (j) gene polymorphism (PTGS1-3) with genotype C/T at position 26793813 of PTGS1 gene, and represented by Reference SNP ID number:rs1213264, (k) gene polymorphism (PTGS1-4) with genotype C/T at position 26794182 of PTGS1 gene, and represented by Reference SNP ID number: rs1213265, (l) gene polymorphism (PTGS1-5) with genotype A/G at position 26794619 of PTGS1 gene, and represented by Reference SNP ID number:rs1213266, (m) gene polymorphism (PTGS2-12) with genotype G/G at position 15697329 of PTGS2 gene, and represented by Reference SNP ID number:rs2745557, (n) gene polymorphism (TAP2-5) with genotype G/G at position 23602539 of TAP2 gene, and represented by Reference SNP ID number:rs2071466, (o) gene polymorphism (IL-4R-14) with genotype C/C at position 18686068 of IL-4R gene, and represented by Reference SNP ID number:rs2234898, and (p) gene polymorphism (IL-4R-29) with genotype T/T at position 18686553 of IL-4R gene, and represented by Reference SNP ID number:rs1801275.

Article 4. A method for evaluating tumor suppression by IFN therapy on a patient with renal cell cancer according to Article 3, wherein the gene polymorphism is any of (a), (f), (h), (n), (o) and (p) of Article 3.

Article 5. A method for evaluating tumor suppression by IFN therapy on a patient with renal cell cancer according to any of Articles 1 to 4, wherein the IFN is selected from the group consisting of natural IFN-α, recombinant IFN-α, and recombinant IFN-γ.

Article 6. A method according to any of Articles 1 to 5, wherein gene polymorphism is determined by at least one method selected from the group consisting of direct sequencing, allele specific oligonucleotide (ASO)-dot blot analysis, single nucleotide primer extension, PCR-single-strand conformation polymorphism (SSCP) analysis, PCR-restriction fragment length polymorphism (RFLP) analysis, invader method, quantitative realtime PCR, and mass array using a mass spectrometer.

Article 7. A method according to Article 6, wherein gene polymorphism is determined by the invader method or direct sequencing.

Article 8. A method according to Article 6, wherein gene polymorphism is determined by the PCR-RFLP analysis.

Article 9. A method according to Article 8, wherein the PCR-RFLP analysis detects, using a restriction enzyme Mspl, a mutation from G to C at 4204027 of intron of human STAT3 gene: rs2293152.

Article 10. A method according to Article 6, wherein gene polymorphism is determined using at least one oligonucleotide selected from the group consisting of (a) to (p) below as a gene polymorphism detection probe or a primer:

(a) an oligonucleotide having a sequence consisting of at least 10 consecutive bases containing a gene polymorphism site with genotype C/T or T/T at position 4243095 of STAT3 gene, and represented by Reference SNP ID number: rs1905341, (b) an oligonucleotide having a sequence consisting of at least 10 consecutive bases containing a gene polymorphism site with genotype C/C at position 4264926 of STAT3 gene, and represented by Reference SNP ID number:rs4796793, (c) an oligonucleotide having a sequence consisting of at least 10 consecutive bases containing a gene polymorphism site with genotype G/G at position 4204027 of STAT3 gene, and represented by Reference SNP ID number:rs2293152, (d) an oligonucleotide having a sequence consisting of at least 10 consecutive bases containing a gene polymorphism site with genotype C/T at position 4050541 of STAT3 (KCNH4) gene, and represented by Reference SNP ID number:rs2293153, (e) an oligonucleotide having a sequence consisting of at least 10 consecutive bases containing a gene polymorphism site with genotype A/C at position 10246541 of SSI3 gene, and represented by Reference SNP ID number:rs2280148, (f) an oligonucleotide having a sequence consisting of at least 10 consecutive bases containing a gene polymorphism site with genotype A/A at position 18686025 of IL-4R gene, and represented by Reference SNP ID number: rs1805011, (g) an oligonucleotide having a sequence consisting of at least 10 consecutive bases containing a gene polymorphism site with genotype A/A at position 17736877 of IRF2 gene, and represented by Reference SNP ID number:rs2797507, (h) an oligonucleotide having a sequence consisting of at least 10 consecutive bases containing a gene polymorphism site with genotype C/C at position 17744613 of IRF2 gene, and represented by Reference SNP ID number:rs796988, (i) an oligonucleotide having a sequence consisting of at least 10 consecutive bases containing a gene polymorphism site with genotype A/A or A/C at position 390141 of ICSBP gene, and represented by Reference SNP ID number: rs2292982, (j) an oligonucleotide having a sequence consisting of at least 10 consecutive bases containing a gene polymorphism site with genotype C/T at position 26793813 of PTGS1 gene, and represented by Reference SNP ID number:rs1213264, (k) an oligonucleotide having a sequence consisting of at least 10 consecutive bases containing a gene polymorphism site with genotype C/T at position 26794182 of PTGS1 gene, and represented by Reference SNP ID number:rs1213265, (l) an oligonucleotide having a sequence consisting of at least 10 consecutive bases containing a gene polymorphism site with genotype A/G at position 26794619 of PTGS1 gene, and represented by Reference SNP ID number:rs1213266, (m) an oligonucleotide having a sequence consisting of at least 10 consecutive bases containing a gene polymorphism site with genotype G/G at position 15697329 of PTGS2 gene, and represented by Reference SNP ID number:rs2745557, (n) an oligonucleotide having a sequence consisting of at least 10 consecutive bases containing a gene polymorphism site with genotype G/G at position 23602539 of TAP2 gene, and represented by Reference SNP ID number:rs2071466, (o) an oligonucleotide having a sequence consisting of at least 10 consecutive bases containing a gene polymorphism site with genotype C/C at position 18686068 of IL-4R gene, and represented by Reference SNP ID number:rs2234898, and (p) an oligonucleotide having a sequence consisting of at least 10 consecutive bases containing a gene polymorphism site with genotype T/T at position 18686553 of IL-4R gene, and represented by Reference SNP ID number:rs1801275.

Article 11. A method according to Article 6, wherein the gene polymorphism detection primer pair is any of (a) to (p) below:

(a) A pair of oligonucleotide primers consisting of the sequences represented by SEQ ID Nos. 1 and 17, (b) A pair of oligonucleotide primers consisting of the sequences represented by SEQ ID Nos. 2 and 18, (c) A pair of oligonucleotide primers consisting of the sequences represented by SEQ ID Nos. 3 and 19, (d) A pair of oligonucleotide primers consisting of the sequences represented by SEQ ID Nos. 4 and 20, (e) A pair of oligonucleotide primers consisting of the sequences represented by SEQ ID Nos. 5 and 21, (f) A pair of oligonucleotide primers consisting of the sequences represented by SEQ ID Nos. 6 and 22, (g) A pair of oligonucleotide primers consisting of the sequences represented by SEQ ID Nos. 7 and 23, (h) A pair of oligonucleotide primers consisting of the sequences represented by SEQ ID Nos. 8 and 24, (i) A pair of oligonucleotide primers consisting of the sequences represented by SEQ ID Nos. 9 and 25, (j) A pair of oligonucleotide primers consisting of the sequence represented by SEQ ID Nos. 10 and 26, (k) A pair of oligonucleotide primers consisting of the sequences represented by SEQ ID Nos. 11 and 27, (l) A pair of oligonucleotide primers consisting of the sequences represented by SEQ ID Nos. 12 and 28, (m) A pair of oligonucleotide primers each consisting of the sequence represented by SEQ ID Nos. 13 and 29, (n) A pair of oligonucleotide primers consisting of the sequences represented by SEQ ID Nos. 14 and 30, (o) A pair of oligonucleotide primers consisting of the sequences represented by SEQ ID Nos. 15 and 31, and (p) A pair of oligonucleotide primers consisting of the sequences represented by SEQ ID Nos. 16 and 32.

Effects of the Invention

The present invention provides a method for detecting an identification marker responsive to IFN therapy for renal cell cancer, in particular the method comprising detecting a specific human gene polymorphism or genotype from a specimen of a patient with renal cell cancer, and evaluating IFN treatment response (tumor-suppression effect) of said patient, a kit therefor, and gene polymorphisms, genotypes, and genotype detection probes and primers used in the method and kit. They are useful for determining drug selection priority in the practice of order-maid medicine for individual patients.

BEST MODE FOR CARRYING OUT THE INVENTION

The abbreviations for amino acids, peptides, base sequences, nucleic acids, etc. used in the present specification are in conformity with IUPAC-IUB regulations (IUPAC-IUB communication on Biological Nomenclature, Eur. J. Biochem., 138:9(1984)), ("Enki-hairetsu mataha aminosan-hairetsu wo fukumu meisaisho nado no sakusei no tameno gaidorain" (Guidelines for preparation of specifications containing base sequences or amino acid sequences" (compiled by Japan Patent Office)), and standard denotations used in the related fields.

"Gene polymorphism" and "polymorphism" used in the present specification refer to a plurality of allele groups occupying a locus or an individual allele in such groups. Among these polymorphisms, those with only one nucleotide being different are termed single nucleotide polymorphisms, or SNP. Single nucleotide polymorphism is abbreviated to "SNP" in the present specification.

Haplotype indicates type of the above gene polymorphisms (SNPs), expressed based on kinds and numbers of alleles in a plurality of SNP sites in continuous gene regions or gene groups.

In the present specification, genotype refers to status of alleles at a genetic locus of a given gene polymorphism site. The genotype of SNP at 4243095 position in STAT3 gene (STAT3-2) is, for example, expressed as C/T heterozygous or T/T homozygous. This is also expressed as "STAT3-2 C/T or T/T". When a patient has genotype STAT3-2 C/T or T/T, the patient is predicted to be likely to respond (PR: paratial response), or to respond well (CR: complete response) to IFN therapy for renal cell cancers (tumor-suppression effect). Therefore, genotype STAT3-2 C/T or T/T can be used as identification markers responsive to IFN therapy for renal cel caners.

The genomic sequences of human genes indicated in the present specification accord with nucleic acid sequences registered under GenBank accession numbers (e.g.: NT_010641) at the nucleic acid sequence data bank of NCBI (National Center for Biotechnology Information). Site information and nucleic acid mutation information of SNPs referred to as human gene polymorphisms in the present invention are similarly found under Reference SNP ID numbers (e.g.: rs1213265) at SNP data bank of NCBI (see Reference SNP (refSNP) Cluster Report, searchable at http://www.ncbi.nlm.nih.gov/SNP). SNP information used in the present specification are also indicated in accordance with Reference SNP ID numbers.

Table 1 shows general information on gene sequences, mRNA sequences, and SNP sites and nucleic acid mutation, obtained from GenBank.

TABLE 1

| Gene | rs# | Nucleic acid | Contig accession | Contig position | mRNA | mRNA Orientation | Protein |
|---|---|---|---|---|---|---|---|
| STAT3-2 | rs1905341 | C/T | NT_010755 | 4243095 | NM_003150 | reverse | |
| STAT3-3 | rs4796793 | G/C | NT_010755 | 4264708 | — | | — |
| STAT3-18 | rs2293153 | C/T | NT_010755 | 4050541 | NM_012285 | reverse | NP_036417 |
| STAT3-17 | rs2293152 | G/C | NT_010755 | 4204027 | NM_003150 | reverse | NP_003141 |
| SSI3-1 | rs2280148 | A/C | NT_010641 | 10246541 | | | |
| IL-4R-14 | rs2234898 | A/C | NT_010393 | 18686068 | NM_000418 | forward | NP_000409 |
| IL-4R-29 | rs1801275 | C/T | NT_010393 | 18686553 | NM_000418 | forward | NP_000409 |
| IL-4R-22 | rs1805011 | C/A | NT_010393 | 18686025 | NM_000418 | forward | NP_000409 |
| IRF2-67 | rs2797507 | A/C | NT_022792 | 17736877 | NM_002199 | reverse | NP_002190 |
| IRF2-82 | rs796988 | C/T | NT_022792 | 17744613 | NM_002199 | reverse | NP_002190 |
| ICSBP-38 | rs2292982 | A/C | NT_019609 | 390141 | NM_002163 | forward | NP_002154 |
| PTGS1-3 | rs1213264 | C/T | NT_008470 | 26793813 | NM_080591 | forward | NP_542158 |
| PTGS1-4 | rs1213265 | C/T | NT_008470 | 26794182 | NM_080591 | forward | NP_542158 |
| PTGS1-5 | rs1213266 | A/G | NT_008470 | 26794619 | NM_080591 | forward | NP_542158 |
| PTGS2-12 | rs2745557 | A/G | NT_004487 | 15697329 | NM_000963 | reverse | NP_000954 |
| TAP2-5 | rs2071466 | G/A | NT_007592 | 23602539 | NM_018833 | reverse | NP_061313 |

| Gene | Site | dbSNP allele | Amino Acid residue | Codon site | Amino acid sequence info | Remarks |
|---|---|---|---|---|---|---|
| STAT3-2 | untranslated | | | | | |
| STAT3-3 | Locus | | | | | |
| STAT3-18 | Intron | | | | | KCNH4 |
| STAT3-17 | intron | | | | | |
| SSI3-1 | locus | | | | | |
| IL-4R-14 | synonymous | T | Leu [L] | 3 | 414 | |
| | contig reference | T | Leu [L] | 3 | 433 | |
| IL-4R-29 | nonsynonymous | G | Arg [R] | 2 | 576 | |
| | contig reference | A | Gln [Q] | 2 | 576 | |

TABLE 1-continued

| | | | | | | |
|---|---|---|---|---|---|---|
| IL-4R-22 | nonsynonymous | C | Ala [A] | 2 | 400 | |
| | contig | A | Glu [E] | 2 | 400 | |
| | reference | | | | | |
| IRF2-67 | intron | | | | | |
| IRF2-82 | intron | | | | | |
| ICSBP-38 | intron | | | | | |
| PTGS1-3 | intron | | | | | |
| PTGS1-4 | intron | | | | | |
| PTGS1-5 | intron | | | | | |
| PTGS2-12 | intron | | | | | |
| TAP2-5 | intron | | | | | |

In Table 1, the column under Gene shows names of the genes on which SNPs the present inventors found are contained, followed by SNP numbers arbitrarily assigned by the inventors. In the table, "rs#" indicates accession numbers for Reference SNPs, "Nucleic acid" indicates nucleic acid mutation (A/G means SNP in which an A is changed to a G), "Contig accession" indicates accession numbers for genomic contig sequence, "Contig Position" indicates position numbers denoting the position of nucleic acid mutation in a genomic sequence, "mRNA" indicates accession numbers for mRNA sequence numbers, and "mRNA orientation" indicates the orientation of mRNA containing gene polymorphism sequences. Further, "Protein" indicates accession numbers for protein sequences, "Location" indicates site information on which gene polymorphisms are present, "dbSNP allele" indicates nucleic acid information on alleles on complement double strands, "amino acid residue" indicates those changed (substituted), "Codon site" indicates information on codon site orders for amino acids coded by nucleic acid, "amino acid sequence information" indicates information on sites of amino acid sequences, and "Remarks" indicates synonyms of genes.

As shown in Table 1, amino acid substitutions caused by specific human gene polymorphisms used in the method of the present invention are identified only in gene polymorphisms relevant to IL-4R, and amino acid substitutions are not caused by gene polymorphisms of other genes.

The term "gene" used in the present specification encompasses not only double stranded DNAs, but also single stranded DNAs (sense strand and antisense strand) composing double stranded DNAs. More specifically, unless otherwise stated, genes (DNAs) according to the present invention encompass double stranded DNAs including human genomic DNAs, single stranded DNAs (sense strand) including cDNAs, single stranded DNAs with sequences complementary to said sense strand, and fragments thereof. Further, said genes (DNAs) can include regulatory region, coding region, exon, and intron. Polynucleotides encompass RNA and DNA. DNA encompass cDNA, genomic DNA and synthetic DNA. Polypeptides include fragments, homologues, derivatives, and variants thereof. Further, variants refer to allele variants naturally occur, those that do not naturally occur, those that are modified (deletion, substitution, addition and insertion), and polynucleotide sequences that do not substantially change functions of encoding polypeptides. Modifications of amino acid sequences can naturally occur by, for example, mutation, and post-translational modification, or alternatively, the modiciation can be artificially caused using naturally occurred genetic elements.

The present invention is accomplished based on the findings that gene polymorphism containing a genotype at a given site of human genes (IFN genes, genes reportedly relevant to IFN-γ signal transduction system, and genes reportedly showing gene expression changes by IFN addition/administration), particularly SNP or SNPs, is strongly correlated with tumor-suppression effects of IFN therapy on a patient with renal cell cancer, and the detection of such gene polymorphism (a genotype at a given site) enables evaluation of the IFN therapy response of a patient with renal cell cancer. In other words, the present invention is accomplished based on the finding that certain human gene polymorphisms, particularly specific SNPs, can be used as evaluation markers for IFN therapy response to renal cell cancers. According to the present invention, the detection of specific SNPs from a specimen of a patient with renal cell cancer enables the prediction of IFN therapy response of the patient with renal cell cancer.

The present invention essentially requires the detection of specific human gene polymorphisms from a specimen of a patient with renal cell cancer, i.e., gene polymorphisms (genotypes) consisting of STAT3-2, STAT3-3, STAT3-17, STAT3-18, SSI3-1, IL-4R-14, IL-4R-22, L-4R-29, IRF2-67, IRF2-82, ICSBP-38, PTGS1-3, PTGS1-4, PTGS1-5, PTGS2-12, and TAP2-5.

SNPs to be detected (typed) by the method of the present invention, i.e., gene polymorphisms (or genotypes) correlative with the tumor-suppression effects of IFN therapy on a patient with renal cell cancer, are more specifically those shown in (a) to (p) below.

(a) gene polymorphism (STAT3-2) with genotype C/T or T/T at position 4243095 of STAT3 gene, and represented by Reference SNP ID number:rs1905341, (b) gene polymorphism (STAT3-3) with genotype C/C at position 4264926 of STAT3 gene, and represented by Reference SNP ID number:rs4796793, (c) gene polymorphism (STAT3-17) with genotype G/G at position 4204027 of STAT3 gene, and represented by Reference SNP ID number:rs2293152, (d) gene polymorphism (STAT3-18) with genotype C/T at position 4050541 of STAT3 (KCNH4) gene, and represented by Reference SNP ID number:rs2293153, (e) gene polymorphism (SSI3-1) with genotype A/C at position 10246541 of SSI3 gene, and represented by Reference SNP ID number:rs2280148, (f) gene polymorphism (IL-4R-22) with genotype A/A at position 18686025 of IL-4R gene, and represented by Reference SNP ID number:rs1805011, (g) gene polymorphism (IRF2-67) with genotype A/A at position 17736877 of IRF2 gene, and represented by Reference SNP ID number:rs2797507, (h) gene polymorphism (IRF2-82) with genotype C/C at position 17744613 of IRF2 gene, and represented by Reference SNP ID number:rs796988, (i) gene polymorphism (ICSBP-38) with genotype A/A or A/C at position 390141 of ICSBP gene, and represented by Reference SNP ID number: rs2292982, (j) gene polymorphism (PTGS1-3) with genotype C/T at position 26793813 of PTGS1 gene, and represented by Reference SNP ID number:rs1213264, (k) gene polymorphism (PTGS1-4) with genotype C/T at position 26794182 of PTGS1 gene, and represented by Reference SNP ID number: rs1213265, (l) gene polymorphism (PTGS1-5) with genotype A/G at position 26794619 of PTGS1 gene, and represented by Reference SNP ID number:rs1213266, (m) gene polymorphism (PTGS2-12) with genotype G/G at position 15697329 of PTGS2 gene, and represented by Reference SNP ID number:rs2745557, (n) gene polymorphism (TAP2-5) with genotype G/G at position 23602539 of TAP2 gene, and represented by Reference SNP ID number:rs2071466, (o) gene polymorphism (IL-4R-14) with genotype C/C at position 18686068 of IL-4R gene, and represented by Reference SNP ID number:rs2234898, and (p) gene polymorphism (IL-4R-29) with genotype T/T at position 1868553 of IL-4R gene, and represented by Reference SNP ID number:rs1801275.

According to the present invention, the detection of specific human gene polymorphisms (SNPs and haplotypes) and/or genotypes can provide information and a means useful for understanding and elucidating tumor-suppression effects and mechanisms (tumor-suppression effects of IFN) on renal cell cancers, predictive diagnosis of renal cell cancer treatment, etc. Further, according to the present invention, such detection can provide valid information to determine treatment protocol for renal cell cancer patients, particularly important information to determine whether or not IFN should be administered as a treatment protocol in the practice of custom-made medicine tailored to an individual renal cell cancer patient.

In the present invention, examples of IFN used in IFN therapies for patients with renal cell cancers include natural IFN-α, recombinant IFN-α, and recombinant IFN-γ, etc. These IFNs can be included in the methods of the present invention not only when used singly, but also when used in combination with immunotherapy drugs, chemotherapy drugs, etc.

Obtention of Human Genes Containing Gene Polymorphisms (SNPs)

The present invention is described in details below. In the present invention, gene samples from a patient with renal cell cancer are first obtained as specimen (step i). The obtained gene samples contain specific gene polymorphisms (SNPs), more specifically, any of the aforementioned gene polymorphisms (a) to (p). Usable examples of such samples are cDNA and genomic DNA extracted from a patient with renal cell cancer, by a conventional method. The sample may be a complementary strand of DNA containing the above-mentioned gene polymorphisms.

Examples of origin of cDNA or genomic DNA samples can include various cells, tissues, cultured cells derived therefrom, etc. More specific examples include body fluids such as blood, saliva, lymph, respiratory tract mucus, urine, sperm, etc. Samples derived from the above origins as specimen are preferably from DNA or genomic DNA of a patient before IFN administration (particularly, including cases wherein any drug is administered at all, in addition to cases wherein drugs other than IFN have already been administered). RNA isolation, mRNA isolation and purification, cDNA synthesis, and cloning from these original samples can be performed in accordance with standard methods.

In the method of the present invention, genomic sequence of specific human genes or complementary strands thereof (e.g. genes or complementary strands thereof containing any of the above gene polymorphisms (a) to (p) (SNPs)) from the above gene samples are prepared (step ii).

The preparation can be readily performed with reference to specific sequence information on genes containing any of the above SNPs (a) to (p) disclosed in the present specification by following common genetic engineering technique [*Molecular Cloning*, $2^{nd}$ edition, Cold Spring Harbor Lab. Press (1989); *Zoku Seikagaku Jikken Koza: Idenshi Kenkyuho I, II, III* ("Biochemistry Experiment Lecture Part II: Gene Studies I, II, III"), compiled by The Japanese Biochemical Society (1986), etc.]. Specifically, the preparation from cDNA or genomic DNA extracted from a renal cell cancer patient having any gene polymorphisms of (a) to (p) described above can be carried out using a suitable probe or restriction enzyme for any of specific genotypes (a) to (p) by following standard methods (e.g. see *Proc. Natl. Acad. Sci., U.S.A.*, 78,6613 (1981); *Science*, 222,778 (1983), etc.) More specifically, the preparation can be achieved by preparing a probe containing a genotype site capable of selectively binding to DNA sequences of desired SNPs, and performing single nucleotide primer extension, invader method, quantitative realtime PCR, or the like, using such a probe.

Usable screening primers are forward primers and reverse primers that are designed based on the nucleic acid sequence information of desired genes. These primers can be synthesized by following standard methods using, for example, an automatic synthesizer. Such screening probes are typically labeled; however, non-labeled probes may be used as long as they are directly or indirectly capable of specifically binding to a labeled ligand. Labeling agents and technique for the probes and ligands are well-known in the related technical fields. Examples include radioactive reagents that can be transferred by nick translation, random priming, kinase treatment, etc., biotin, fluorescent dyes, chemiluminescent reagent, luciferase and like enzymes, antibodies, or the like.

Extracted DNA or mRNA can be amplified by gene amplification methods. By amplification, easier and more accurate detection can be achieved by the method of the present invention. Examples of gene amplification methods include PCR method (Saiki, R. K., Bugawan, T. L. et al., *Nature*, 324, 163-166 (1986)), NASBA method (Comptom, J., *Nature*, 650, 91-92 (1991)), TMA method (Kacian, D. L., and Fultz, T. J., U.S. Pat. No. 5,399,491 (1995)), SDA method (Walker, G. T., Little, M. C. et al., *Proc. Natl. Acad. Sci., U.S.A.*, 89, 392-396 (1992)), etc.

The isolation and purification of gene fragments amplified by PCR method, etc. can be performed by gel electrophoresis or using a column. These performances can be verified by, for example, mass-spectral method or gel agarose electrophoresis. Genes amplified by these methods are subjected to the detection of gene polymorphisms (a) to (p) (SNPs) of the present invention (SNP typing) according to the property of the gene amplified.

SNP Typing

According to the method of the present invention, DNA in a given gene region of the above specimen is sequenced and analyzed, and SNPs thereof are detected (SNP typing) (step iii). The typing can be carried out by methods (1) to (8) below.

(1) Nucleotide Direct Sequencing

Gene polymorphisms can be detected by DNA sequencing of a given gene, by following nucleotide direct sequencing methods routinely employed to determine nucleic acid sequences in this type of gene, such as dideoxy method (Sanger et al., *Proc. Natl. Acad. Sci., U.S.A.*, 74, 5463-5467 (1977)), Maxim-Gilbert method (*Methods in Enzymology*, 65, 499 (1980)), etc. Gene polymorphisms can also be detected effectively by combination of the nucleotide direct sequencing method and a DNA amplification method such as PCR method. In particular, a combined method of PCR method or a DNA amplification equivalent thereto and such a direct sequencing method is preferably carried in view of convenient and easy operation as well as sensitive and accurate detection achieved, despite a small amount of DNA sample required.

Such a preferable method can basically be performed by, for example, subjecting gene fragments amplified by PCR method or purified products thereof to direct sequencing in accordance with dideoxy method, Maxum-Gilbert Method, etc. Alternatively, such a method can be readily achieved by determining nucleotide sequence using a commercial sequence kit. Thus, presence/absence of SNPs at the aforementioned given positions of specific human genes can be detected.

DNA fragments to be amplified by PCR in the methods above and hereinafter are not limited as long as they contain at least one particular site on which variations mentioned earlier are presumably found. Usable DNA fragments typically consist of about 50 to about several thousand bases, and more preferably about 50 to about several hundred bases.

(2) Allele Specific Oligonucleotide (ASO)-Dot Blot Analysis

Another method for detecting polymorphisms on specific genes is that following allele specific oligonucleotide (ASO)-dot blot analysis (Conner, B. J. et al., *Proc. Natl. Acad. Sci., U.S.A.*, 80, 278-282 (1983)). This method can be performed by subjecting a DNA fragment hybridizable with oligonucleotide probes specific to an allele of a PCR amplified gene fragment, using forward primers and reverse primers designed so as to sandwich a target SNP, to dot blot analysis. In this way, the SNP on such DNA fragments can be detected.

(3) Single Nucleotide Primer Extension

Polymorphism detection on specific genes can also be achieved by an approach based on single nucleotide primer extensions such as SNaPshot method, pyrosequencing, and point mutation detection, which was disclosed in Unexamined Japanese Patent Publication No. 2000-279197. In these methods, a probe designed so as to match the sequence immediately or several bases before a target SNP, i.e., the probe designed so that the 3' end thereof is positioned on one base upstream of or close to the detection target mutation, is annealed to a DNA specimen. These methods can be performed using a commercial SNPs detection kit and a software accompanied thereto.

For example, SnaPshot method can be carried out using ABI PRISM SnaPshot ddNTP Primer Extension Kit (manufactured by Applied Biosystems). SNPs can be typed by using fluorescent fragments produced after the reaction on ABI PRISM310/377/3100/3700DNA Analyzer (all manufactured by Applied Biosystems) and GeneScan software.

Pyrosequencing can be carried out as follows. Genomic DNA is isolated from blood sample, etc. by following a standard manner, from dozens to several hundreds of bases containing mutations are PCR-amplified using biotin-labeled primer, a single stranded DNA is purified using magnetic beads, and the purified DNA is used as specimen. Annealed to this specimen is a primer which is designed so as to sequence from several bases upstream of a target gene polymorphism, and then one kind of dNTP at a time is added thereto in accordance with the sequence close to the gene polymorphism entered in a software, thereby causing a reaction. Since pyrophosphate (PPi) is formed when DNA polymerase extends nucleic acids, PPi produces ATP by sulfurylase. Luminescence emitted by a reaction of luciferase to this ATP substrate is determined using a Luminescence detector, CCD camera, etc. Thus, target gene typing becomes feasible by the peak analysis of the Luminescence emitted according to added dNTPs. This method enables 96 samples to typed in about 15 minutes.

Common reagents and apparatus can be used in the above method. Examples of usable reagents include enzyme mixture consisting of DNA polymerase, ATP-sulfurylase, luciferase, and apyrase, substrate liquid consisting of luciferin and APS (adenosine 5' phosphate sulfate), commercial SNP reagent kits comprising dNTP as a component consisting of dATP (deoxyadenosine triphosphate), dCTP, dGTP and dTTP (manufactured by Pyrosequencing AB), etc. Examples of usable apparatus include PSQ96 system for automatic DNA sequence analysis (Pyrosequencing AB) and SNP software for using the system (Pyrosequencing AB).

Pyrosequencing can be performed in accordance with the description in U.S. Pat. No. 6,159,693 specification, i.e. nucleic acid is isolated and amplified by PCR, the amplified PCR products are purified, and reacted with pyrophosphate using READIT™ System (Promega Corporation), thereby analyzing the obtained data. A commercial Excel program using READIT technology (Promega Corporation) can be employed for such a data analysis.

(4) PCR-Single-Strand Conformation Polymorphism (SSCP) Analysis

Further, gene polymorphism detection by the method of the present invention can be achieved by PCR-SSCP analysis (Orita, M., Iwahara, H. et al., *Proc. Natl. Acad. Sci., U.S.A.*, 86, 2776-2770 (1989)). In this method, PCR amplified products (single-stranded DNA) are subjected to non-denaturing polyacrylamide gel electrophoresis, thereby identifying the presence or absence of a single nucleotide polymorphism based on the differences each PCR product has migrated.

(5) PCR-Restriction Fragment Length Polymorphism (RFLP) Analysis

For the detection of SNPs or haplotypes on specific genes of the present invention, when a nucleic acid sequence containing a detection target polymorphism also contains a restriction enzyme recognitions site, the detection can be accomplished by restriction fragment length polymorphism (RFLP) analysis (Botstein, D. R. et al., *Am. J. Hum. Gen.*, 32, 314-331 (1980)).

More specifically, RFLP analysis can be performed as follows, according to genotype at a given site on gene polymorphisms (a) to (p) described above. Taking the genotype at a given site on the gene (c) described above as an example, to detect gene polymorphism with genotype G/G at genomic consequence position 4204027 of STAT3 gene [STAT3-17], RFLP analysis is carried out using a restriction enzyme which recognizes not only the site of the target genotype, but also upstream and downstream of such a site. Enzymes used in RFLP analysis may be various known restriction enzymes that are capable of recognizing the site of the target genotype and the sequences upstream and downstream of such a site. Specific example as such is Mspl.

RFLP analysis is more preferably performed by PCR-RFLP method, i.e. a DNA specimen is amplified and prepared by PCR or modified method thereof beforehand, and mass-prepared and concentrated DNA specimen are subjected to RFLP analysis. Thus, target gene polymorphisms can be detected where sites are specifically cleaved.

According to this gene polymorphism detection method, genomic DNA is first extracted from a human specimen, DNA fragments at a region containing a gene polymorphism site of said gene are amplified by PCR, etc., thereby obtaining concentrated gene samples in a large amount. The amplified DNA specimen are then cleaved using a specific restriction enzyme, and the cleaved DNA are examined (for presence or absence of cleavage, base length of cleaved fragments) by following a standard method.

(6) Invader Method

The SNPs detection of specific genes of the present invention can also be performed by Invader method. Invader method can be achieved in reference to the following documents;

Lyamichev, V. et al., *Nat. Bioltechnol.*, 17(3) 292-296 (1999), and

International Patent Publication No. WO9823774 (Unexamined Patent Publication No. 2001-526526).

The method disclosed in these publications does not require target DNA amplification beforehand to analyze SNPs on genomic DNA, and is carried out as follows.

To detect the presence of SNPs of specific target genes, e.g. the genes described in (a), (b), and (d) to (p), genomic DNA is first isolated, followed by the synthesis of probes using, for example, an automated synthesizer. First a target oligonucleotide probe to be synthesized consisting of 30 to several hundred bases is designed so as to have a 5' flap of 15 to 50 bases, have nucleic acid (SNP in the present invention) to be detected on the 3' end side of said 5' flap, and be complementary to the target genomic DNA excluding the nucleic acid of the target genotype. An invader oligonucleotide probe consisting of 15 or more bases is designed to be complementary to the target genomic DNA, and have nucleic acid complementary to the nucleic acid to be detected at its 3' end. The isolated genomic DNA and an enzyme that cuts the 5' flap of the first probe (flap endonuclease) are simultaneously added to these probes, and reacted in a suitable reaction mixture.

When the genomic DNA in the specimen contains the desired SNP, the first reaction by which the 5' flap having the nucleic acid of the genotype at its 3' end is separated is completed. When the genomic DNA in the specimen does not contain the nucleic acid sequence of the genotype, no cleavage by the above enzyme occurs.

The 5' flap separated from the first probe by the cleavage of the enzyme complimentarily binds to a fluorescence resonance energy transfer (FRET) probe as a target, the 3' end of the 5' flap invades into the FRET probe. Similarly, the above enzyme causes a reaction, thereby separating the fluorescent dye that has been quenched.

FRET probes to be used in the second reaction contain an identical sequence despite being targets to be detected, and are essentially constructed to comprise the following two elements.

(1) 3' region complement to the separated product in the first reaction, and (2) a self-complementary region that forms a duplex to mimic a single stranded probe, and hybridizes together with target, which contains a reporter fluorescent dye and a quencher fluorescent dye.

When the above reporter fluorescent dye is attached to a probe to which the above quencher fluorescent dye is also attached, the reporter dye is quenched due to fluorescence resonance energy transfer. When it is not attached to a probe with the above quencher fluorescent dye, the reporter dye is not quenched. Consequently, when the 5' flap separated from the first probe by cleavage is hybridized to the FRET probe, the flap acts as an invader-oligonucleotide in the second reaction, thereby producing an invaded complex specifically recognized by an enzyme. Thus, the cleavage of the FRET probes by the above specific enzyme separates two fluorescent dyes, and produces detectable fluorescence signals. Gene polymorphisms containing the desired SNPs can be detected by reading such fluorescence signals in a standard fluorescent microtiter plate reader. The fluorescence signals can be amplified from 1 to up to $10^6$ times by combining the first and the second reactions. More specifically, SNP-typing can be performed using two FRET probes of different fluorescent dyes.

(7) Quantitative Realtime PCR

Gene polymorphism detection on specific genes by the present invention can be easily carried out by quantitative real time PCR (TaqMan method).

The method can be performed as follows. To detect gene polymorphisms containing a target SNP, a forward-side primer and a reverse-side primer, each consisting of 15 to 39 bases are prepared to detect a DNA fragment on a suitable region containing the polymorphism (nucleic acid site). However, the forward-side primer and the reverse-primer are designed so as not to contain the target nucleic acid site (single nucleotide genotype). A probe, which is an oligonucleotide having a base sequence consisting of 15 to 50 bases with a reporter fluorescent dye and a quencher fluorescent dye attached thereto, is then produced. The base sequence of such a probe must be selected so that the hybridization region of the forward-side primer does not overlap with the hybridization region of the probe. The probe is designed so as to have a sequence complementary to the sequence specific to an allele for detecting the presence/absence of the target single nucleotide genotype. Using such a probe, a given gene to be detected in a specimen, e.g. a DNA fragment of interest in the genes described in the aforementioned (a) to (p), are amplified by PCR, and resulting fluorescent output from the reaction mixture is measured real-time. SNP typing is thus achieved. More specifically?, the SNP detection (typing) can be performed using two probes of different fluorescent dyes.

Preferable examples of the reporter fluorescent dye used in the above invader assay and TaqMan method include fluorescein type fluorescent dyes such as FAM (6-carboxyfluorescein), and preferable example of the quencher fluorescent dye include rhodamine type fluorescent dyes such as TAMRA (6-carboxy-tetramethyl-rhodamine). These fluorescent dyes are well known, and hence included in commercial real time-PCR kits for convenient use. Binding sites for the reporter fluorescent dye and the quencher fluorescent dye are not limited, but typically the reporter fluorescent dye binds to one end (preferably 5' end) of an oligonucleotide probe, and the quencher fluorescent dye binds to the other end. A method for binding a fluorescent dye to oligonucleotides is already known, and disclosed in publications such as Noble et al., (1984), *Nuc. Acids Res.*, 12: 3387-3403, and Iyer et al., (1990), *J. Ame. Chem. Soc.*, 112: 1253-1254.

TaqMan method itself is a known method, and devices and kits designed for use in the method are marketed. In the present invention, these commercial devices and kits can also be used. When these commercial devices and kits are used, the method of the present invention is performed following the procedures disclosed in U.S. Pat. No. 2,825,976, or the user manual for ABI PRISM 7700 Sequence Detection System manufactured by PE Biosystems.

(8) Mass Array Using a Mass Spectrometer

Mass array method detects a mass difference caused by polymorphisms. More specifically, a region containing a polymorphism to be detected is amplified by PCR, an extension primer is hybridized immediately before a SNP position, and an extension reaction is carried out using a ddNTP/dNTP mixture-containing reaction mixture, e.g. reaction mixture containing ddATP, dCTP, dGTP and dTTP, thereby producing fragments with different 3' ends according to SNPs. These products are purified and subjected to MALDI-TOF mass spectrometer for analysis, thereby determining correlation between molecular mass and genotype (Pusch, W., Wurmbach, J H., Thiele, H., Kostrzewa, M., *MALDI-TOF mass spectrometry-based SNP genotyping, Pharmacogenomics*, 3(4): 537-48 (2002)). The method can easily be performed using, e.g. Sequenom's MassArray High-throughput SNP detection system.

(9) Other Typing Methods

The SNPs typing of the genes used in the method of the present invention can also be performed by various known methods including those for sequencing DNA and those for detecting gene polymorphisms and gene mutations. Examples of these methods are given below.

(9-1) PCR-SSO (Sequence-Specific Oligonucleotide) Typing

SNP-corresponding solid-phased probes on a carrier are hybridized to a specimen (gene amplified product), thereby determining the efficiency difference of the hybridization based on the presence/absence of mismatches.

(9-2) PCR-SSP Typing for Detecting Point Mutation

Using a primer specific to a sequence for gene amplification with a base matching a point mutation designed at its 3' end, this typing takes advantage of a remarkable difference in PCR amplification efficiency depending on whether the 3' end of the primer is complementary or not.

(9-3) PCR-DGGE (Denaturing Gradient Gel Electrophoresis) Analysis

A gene polymorphism-containing DNA fragment and a wild-type DNA fragment are mixed for hybridization, and subsequently subjected to electrophoresis in polyacrylamide gel, wherein concentrations of denaturing agents such as urea, formamide, etc. get gradually higher. The resulting DNA fragments dissociate to single stranded DNAs at a position where concentration of denaturing agents is lower, compared with homogenous double stands with no mismatches. Since the single stranded DNA has faster electrophoretic mobility than that of the double stranded DNA, single base polymorphism (difference) can be detected based on the migration rate difference between the DNA strands.

(9-4) PCR-DGGE/GC Clamp (Shefield, V. C. et al., *Proc. Natl. Acad. Sci., U.S.A.*, 86, 232-236 (1989))

In addition to the above PCR-DGGE analysis, this method compensates a drawback of incomplete detection in case a plurality of base substitutions, deletions, additions or insertions are caused, by coupling a region with a high GC content to a DNA fragment containing gene polymorphism nucleic acid to be detected. The method necessitates a step of adding a GC clamp to a DNA fragment containing a gene polymorphism to be detected.

(9-5) RNase Protection Assay (Finkelstein, J. et al., *Genomics*, 7, 167-172 (1990))

(9-6) In Situ RT-PCR (*Nucl. Acids Res.*, 21, 3159-3166 (1993))

(9-7) In Situ Hybridization (9-8) Southern blotting (Sambrook, J. et al., *Molecular Cloning a Laboratory Manual.*, Cold Spring Harbor Laboratory Press, NY (1989)

(9-9) Dot Hybridization Assay (Southern, E. M., *J. Mol. Biol.*, 98: 503-517 (1975), etc.)

(9-10) Fluorescence In Situ Hybridization (FISH: Takahashi, E. et al., *Hum. Genet.*, 86, 1416 (1990))

(9-11) Comparative Genomic Hybridization (CGH: Kallioneimi, A. et al., *Science*, 258, 818-821 (1992)), and Spectral Karyotyping (SKY: Rowley, J. D. et al., *Blood*, 93, 2038-2042 (1999)).

(9-12) A Method Using a Clone of Yeast Artificial Chromosome (YAC) Vector as a Probe (Lengauer, C. et al., *Cancer Res.*, 52, 2590-2596 (1992)).

SNPs and haplotypes of human genes are thus detected by the method of the present invention.

According to the method for predicting response of renal cell cancer patients to IFN therapy by the present invention, when a polymorphism of human gene, an indication (marker), detected by the above method is identified in the specimen, the specimen is expected to be highly responsive to the IFN therapy (step iv).

For patients whose response to IFN therapy is determined to be high, selection of IFN is prioritized at the drug selection stage for renal cell cancers due to its predicted good therapeutic effects. This leads to the suppression of unnecessary drug administration to patients, whereby side effects caused by drugs are diminished.

In particular, gene polymorphisms or genotypes of the human genes detected by the method according to the present invention are highly relevant to IFN therapy effect (tumor-suppression effect) on renal cell cancers. Consequently, the detection result enables the practice of order-made medicine for individual patients with renal cell cancer, i.e. a medical therapy in which the most effective drugs for individual patients are suitably selected.

Oligonucleotide

The present invention further provides oligonucleotides used as probes or primers for detecting gene polymorphisms in the evaluation (detection) method of the present invention. Such nucleotides are not limited as long as they are capable of specifically amplifying a sequence containing a given human gene polymorphism or genotype region. Such nucleotides can be suitably synthesized and constructed in accordance with a standard manner, based on the sequence information of a given gene polymorphism or genotype.

More specifically, the synthesis can be performed by typical chemical syntheses such as phosphoramidites method, phosphate triester method, etc., using a commercial automatic oligonucleotide synthesizer, e.g. Gene Assembler Plus: Pharmacia LKB), etc. Double stranded fragments can be obtained by synthesizing a chemically-synthesized single-stranded product and a complementary chain thereof, and annealing them under appropriate conditions, or attaching the complementary chain to said single stranded product using suitable primer sequences and DNA polymerase.

Preferable examples of oligonucleotides used as the above probes or primers include oligonucleotides partially matching a DNA fragment designed so as to contain a gene polymorphism sequence of a given gene, and consisting of at least 10, typically about 10 to about 35 consecutive bases. Examples of a primer pair include two oligonucleotide sequences designed and synthesized so as to sandwich an SNP in a DNA sequence of a gene. A DNA fragment containing a gene polymorphism sequence itself can be used as an oligonucleotide probe.

Preferable examples of oligonucleotides used as the above probes include those described in (a) to (p) below. Among the following oligonucleotides, preferable probes are those with a sequence consisting of at least 15 consecutive bases, including a polymorphism region of a given gene.

(a) an oligonucleotide having a sequence consisting of at least 10 consecutive bases containing a gene polymorphism site with genotype C/T or T/T at position 4243095 of STAT3 gene, and represented by Reference SNP ID number: rs1905341, (b) an oligonucleotide having a sequence consisting of at least 10 consecutive bases containing a gene polymorphism site with genotype C/C at position 4264926 of STAT3 gene, and represented by Reference SNP ID number:rs4796793, (c) an oligonucleotide having a sequence consisting of at least 10 consecutive bases containing a gene polymorphism site with genotype G/G at position 4204027 of STAT3 gene, and represented by Reference SNP ID number:rs2293152, (d) an oligonucleotide having a sequence consisting of at least 10 consecutive bases containing a gene polymorphism site with genotype C/T at position 4050541 of STAT3 gene, and represented by Reference SNP ID number:rs2293153, (e) an oligonucleotide having a sequence consisting of at least 10 consecutive bases containing a gene polymorphism site with genotype A/C at position 10246541 of SSI3 gene, and represented by Reference SNP ID number:rs2280148, (f) an oligonucleotide having a sequence consisting of at least 10 consecutive bases containing a gene polymorphism site with genotype A/A at position 18686025 of IL-4R gene, and represented by Reference SNP ID number: rs1805011, (g) an oligonucleotide having a sequence consisting of at least 10 consecutive bases containing a gene polymorphism site with genotype A/A at position 17736877 of IRF2 gene, and represented by Reference SNP ID number:rs2797507, (h) an oligonucleotide having a sequence consisting of at least 10 consecutive bases containing a gene polymorphism site with genotype C/C at position 17744613 of IRF2 gene, and represented by Reference SNP ID number:rs796988, (i) an oligonucleotide having a sequence consisting of at least 10 consecutive bases containing a gene polymorphism site with genotype A/A or A/C at position 390141 of ICSBP gene, and represented by Reference SNP ID number: rs2292982, (j) an oligonucleotide having a sequence consisting of at least 10 consecutive bases containing a gene polymorphism site with genotype C/T at position 26793813 of PTGS1 gene, and represented by Reference SNP ID number:rs1213264, (k) an oligonucleotide having a sequence consisting of at least 10 consecutive bases containing a gene polymorphism site with genotype C/T at position 26794182 of PTGS1 gene, and represented by Reference SNP ID number:rs1213265, (l) an oligonucleotide having a sequence consisting of at least 10 consecutive bases containing a gene polymorphism site with genotype A/G at position 26794619 of PTGS1 gene, and represented by Reference SNP ID number:rs1213266, (m) an oligonucleotide having a sequence consisting of at least 10 consecutive bases containing a gene polymorphism site with genotype G/G at position 15697329 of PTGS2 gene, and represented by Reference SNP ID number:rs2745557, (n) an oligonucleotide having a sequence consisting of at least 10 consecutive bases containing a gene polymorphism site with genotype G/G at position 23602539 of TAP2 gene, and represented by Reference SNP ID number:rs2071466, (o) an oligonucleotide having a sequence consisting of at least 10 consecutive bases containing a gene polymorphism site with genotype C/C at position 18686068 of IL-4R gene, and represented by Reference SNP ID number:rs2234898, and (p) an oligonucleotide having a sequence consisting of at least 10 consecutive bases containing a gene polymorphism site with genotype T/T at position 1868553 of IL-4R gene, and represented by Reference SNP ID number:rs1801275.

Specific examples of the oligonucleotide of the present invention used as the aforementioned primer pairs include, as described later in Examples, those as forward primers with sequence numbers 1 to 16 and reverse primers with sequence numbers 17 to 32 for each of the above genes.

Detection Kit

The detection (evaluation) method of the present invention can be more readily conducted using a reagent kit for the detection of a gene polymorphism or genotype of a given human gene in a specimen. The present invention further provides such a reagent kit.

An example of the kit according to the present invention comprises as an essential component at least a DNA fragment partially or entirely hybridizable to the base sequence of a DNA fragment containing any of the above gene polymorphisms or genotypes of a given human gene or complementary base sequence thereof, or as an essential component at least a DNA fragment hybridizable to a base sequence containing one to several bases upstream from any of the above specific gene polymorphism sites or genotype sites. Another example of the kit according to the present invention comprises as an essential component a restriction enzyme, e.g. Mspl, that recognizes a sequence of several nucleic acids including any of the above specific gene polymorphism sites or genotype sites.

Other components comprised in the kit of the present invention include labeling agents, and reagents required for performing PCR (e.g. TaqDNA polymerase, deoxynucleotide triphosphate, DNA amplification primers, etc.). Examples of labeling agents include chemically modified substances such as radioactive isotopes, light emitting substances, fluorescent substances, etc., and a DNA fragment itself may be conjugated beforehand with such a labeling agent. For convenient measuring, the kit of the present invention may further contain suitable reaction diluent, standard antibody, buffer, wash, reaction stop solution, etc.

Since the gene polymorphisms or genotypes of given genes found by the present inventors are highly relevant to IFN therapy effects (tumor-suppression effect) on renal cell cancers, according to the present invention, suitable selection of more effective drugs for individual patients with renal cell cancer becomes feasible in the practice of order-made medicine. The present invention provides a method for detecting a given human gene polymorphism or genotype as a marker relevant to the effect of IFN therapy on renal cell cancers, i.e., the method for detecting a given gene polymorphism or genotype in a specimen of a patient with renal cell cancer as an identification marker responsive to IFN therapy for renal cell cancers, a diagnostic agent used in such a method, and a kit for diagnosis.

EXAMPLES

The present invention is described in further detail with reference to examples below, but is not limited to them.

Example 1

(1) Specimens for Analysis

Specimens for analysis used in this test are genomic DNA samples extracted from non-tracable, anonymized blood samples after consensuses of subjects were obtained at participating facilities, and samples from which genomic DNAs are already extracted at the participating facilities. Samples without consensus and non-anonymized samples were not used for analysis. Further, subject information (patient background, etc.) was not transmitted to laboratory workers or Otsuka Pharmaceutical Co., Ltd., Theranostics Research Center (hereinafter referred to as "TRC"), a collaborator.

There were 86 registered samples for this test, out of which 76 samples were derived from blood samples, and 10 samples were already prepared as DNA. These samples were collected based on "SNPs analysis in interferon-related genes aiming at investigating predicting factors of IFN-α therapeutic effects on renal cell cancers (Ethical Committee Reception Number: 010724-1)", a research project conducted by Application & Development group upon approval of the Ethical Committee of Otsuka Pharmaceutical Co., Ltd.

This project was performed in compliance with "ETHICS GUIDELINES FOR HUMAN GENOME/GENE ANALYSIS RESEARCH, announced in March 2001 by the Ministry of Education, Culture, Sports, Science and Technology; the Ministry of Health, Labour and Welfare; and the Ministry of Economy, Trade and Industry (the First Notification)".

The collected blood samples were made non-traceable, anonymous at the participating facilities, and transported frozen to TRC. At TRC, genomic DNAs were extracted from these blood samples to use as samples for analysis.

The samples from which genomic DNAs were already extracted were also made non-traceable, anonymous at the participating facilities, and transported frozen to TRC for use.

All genomic DNA samples used in this research were strictly handled and stored in dedicated storage (freezed at 4° C.) in a TRC laboratory during the research period.

(2) Genes for Analysis

Genes for analysis used in this test are the following gene clusters.

(2a) IFN-α Receptor and Signal Transduction System

IFNAR1 (α chain) (interferon alpha receptor 1), IFNAR2 (βL chain) (interferon beta receptor 2), JAK1 (Janus kinase 1, a protein of tyrosine kinase), Tyk2, STAT1 (signal transducer and activator of transcription 1, 91 kDa), STAT2 (signal transducer and activator of transcription 2, 113 kDa), STAT3 (signal transducer and activator of transcription 3, acute-phase response factor), p48 (ISGF3γ, interferon-stimulated transcription factor 3, gamma, 48 kDa), SOCS-1 (suppressor of cytokine signaling 1/SSI-1) (synonyms:JAB, CIS-1, SSI-1), SOCS-2 (suppressor of cytokine signaling 2/STATI2) (synonyms:CIS-2, SSI-2, STATI2), SOCS-3 (suppressor of cytokine signaling 3/SSI-3) (synonyms:CIS-3, SSI-3), Shp-2 (synonyms:PTPN11:protein tyrosine phosphatase, non-receptor type 11 (Noonan syndrome 1)).

(2b) Th1/Th2 System

STAT4 (signal transducer and activator of transcription 4), IL-2 (interleukin 2), IFN-γ (interferon gamma), TNF-α (tumor necrosis factor alpha), TNF-β (tumor necrosis factor beta) (LTA; lymphotoxin alpha, TNF superfamily, member 1), IL-4 (interleukin 4), IL-4 Receptor-α, IL-4 Receptor-β, IL-5 (interleukin 5, colony-stimulating factor, eosinophil), IL-6 (interleukin 6, interferon bate 2), IL-10 (interleukin 10), IL-13 (interleukine 13).

(2c) Genes Whose Expression are Reportedly Changed by IFN-α

PKR (PRKR, protein kinase, interferon-inducible double stranded RNA dependent), IRF1 (IFN-regulatory factor 1), IRF2 (IFN-regulatory factor 2), ICSBP (IFN consensus sequence binding protein), Cox-1 (PTGS1; prostaglandin-endoperoxide synthase 1, prostaglandin G/H synthase and cyclooxygenase), Cox-2 (PTGS2; prostaglandin-endoperoxide synthase 2, prostaglandin G/H synthase and cyclooxygenase), MxA (Mx-1; myovirus (influenza virus) resistance 1, interferon-inducible protein p78 (mouse))

(2d) Other Genes

TAP1 (transporter 1, ATP-binding cassette, sub-family B (MDR/TAP)), TAP-2 (transporter 2, ATP-binding cassette, sub-family B (MDR/TAP)), LMP7 (PSMβ8; proteasome (prosome, macropain) subunit, beta type, 8 (large multifunctional protease 7), CTLA-4 (cytptoxic T-lymphocyte-associated protein 4), GSTT1 (glutathione S-transferase theta 1), VHL, HIF-1α, HLF, VEGF (vascular endothelial growth factor).

(3) SNPs for Analysis

Among the above gene clusters, SNPs registered in dbSNPs of NCBI at the beginning of the test were compared with registered gene sequences for analysis at Bioinformatics room (hereinafter referred to as "BI room") of Otsuka Pharmaceutical Co., Ltd. As a result of this comparison, those mapped close to the registered sequences were used for the analysis of this test, but those that did not map close thereto were excluded from the analysis. The final number of SNPs for analysis were 1167.

(4) Test Procedures (4a) Genomic DNA Extraction

Genomic DNA extraction was conducted using a genome extraction kit from whole blood (PUREGENE™, Gentra Systems, Inc.). The extraction procedures followed the standard protocol accompanied with PUREGENE™. The extracted genomic DNA was lysed in a lysis solution included in the kit, and absorbance was measured to calculate the entire amount extracted.

(4b) PCR (for Invader Assay)

Genomic regions containing SNPs for analysis were amplified by PCR. ExTaq™ (TaKaRa) was used as DNA polymerase, and the accompanying 10× Ex Taq Buffer was used as a reaction buffer.

The reaction was carried out under the conditions below.
Tamplate amount (genomic DNA): 1 to 10 ng
Primer concentration: 0.1 to 0.2 μM
Total reaction mixture volume: 15 μL
PCR cycle: (1) 95° C.×2 min., (2) 95° C.×30 sec., (3) 50 to 64° C.×30 sec., (4) 72° C.×1.5 min., (5) (2) to (4)×50 cycles, and (6) kept at 15° C.

PCR products were used as reaction templates for the Invader Assay below.

The nucleic acid sequences of the forward primers used in the above reaction are shown as represented by sequence numbers 1 to 16, and the nucleic acid sequences of the reverse primers are shown as represented by sequence numbers 17 to 32. Table 2 shows the relationship among primers, given human gene genomes, and SNPs contained therein.

TABLE 2

| Gene | SNPs(rs#) | SNPs(TRC#) | Product Size (bp) | L Primer | R Primer | Restriction Enzyme (recognized RFLP sequence) |
|---|---|---|---|---|---|---|
| STAT3 | Rs1905341 | STAT3-2 | 470 | Seq. No.: 1 | Seq. No.: 17 | x |
|  | Rs4796793 | STAT3-3 | 806 | Seq. No.: 2 | Seq. No.: 18 | x |
|  | Rs2293152 | STAT3-17 | 461 | Seq. No.: 3 | Seq. No.: 19 | RFLP Msp I (TGCSGGA) |
|  | Rs2293153 | STAT3-18 | 276 | Seq. No.: 4 | Seq. No.: 20 | x |
| SSI3 | Rs2280148 | SSI3-1 | 456 | Seq. No.: 5 | Seq. No.: 21 | x |
| IL-4R | Rs1805011 | IL4R-22 | 378 | Seq. No.: 6 | Seq. No.: 22 | x |
| IRF2 | Rs2797507 | IRF2-67 | 382 | Seq. No.: 7 | Seq. No.: 23 | x |
|  | Rs796988 | IRF2-82 | 434 | Seq. No.: 8 | Seq. No.: 24 | x |
| ICSBP | Rs2292982 | ICSBP-38 | 427 | Seq. No.: 9 | Seq. No.: 25 | x |
| PTGS1 | Rs1213264 | PTGS1-3 | 476 | Seq. No.: 10 | Seq. No.: 26 | x |
|  | Rs1213265 | PTGS1-4 | 436 | Seq. No.: 11 | Seq. No.: 27 | x |
|  | Rs1213266 | PTGS1-5 | 411 | Seq. No.: 12 | Seq. No.: 28 | x |
| PTGS2 | Rs2745557 | PTGS2-12 | 486 | Seq. No.: 13 | Seq. No.: 29 | x |
| TAP2 | Rs2071466 | TAP2-5 | 475 | Seq. No.: 14 | Seq. No.: 30 | x |
| IL-4R | Rs2234898 | IL4R-14 | 432 | Seq. No.: 15 | Seq. No.: 31 | x |
|  | Rs1801275 | IL4R-29 | 491 | Seq. No.: 16 | Seq. No.: 32 | x |

(5) Invader Assay

The PCR products containing amplified SNP regions were diluted 10 to 1000 times in distilled water, the diluted PCR products were denatured to obtain single stranded DNAs by heating at 95° C. for 5 minutes, followed by immediate cooling on ice. The resulting DNAs, used as reaction templates, were mixed with a reagent for invader assay to prepare reaction mixtures. The compositions of the reaction mixtures were in compliance with the accompanying protocol 384-WELL REACTION FORMAT.

The reaction mixtures were incubated at 63° C. for 30 to 60 minutes, and reacted with an enzyme. After the reaction, two wavelengths (red and green), excitation light 485±6 nm, emitted light 530±6 nm (FAM dye), and excitation light 560±6 nm, emitted light 620±6 nm, were used to measure fluorescence intensities, using a fluorescence microplate reader, Safire (TECAN).

All typing procedures, except the dilution, were performed using a Biomek FX/SAMI (Beckman Coulter)-based SNPs automated typing system.

The measurement results of the fluorescence intensities were entered into BARCODE LAB SYSTEM, version 1.0 equipped with automatic typing correction (BLABS™, Mitsui Knowledge Industry Co., Ltd.), and SNP genotyping was determined by automatic typing. The typing results were identified again using a scatterplot by researchers.

(6) PCR-RFLP

SNPs that could not be typed by invader assay were typed by PCR-RFLP. In this method, SNPs are typed based on cleavage of a SNP-containing region by a restriction enzyme. When a SNP region did not contain a suitable site recognized by a restriction enzyme, a restriction enzyme recognizable site was formed by designing amplification primers close to the SNP, and intentionally changing the sequences of the primers.

In this method, restriction enzyme Nspl was used to detect SNPs on STAT3-17.

PCR was performed using Vogelstein buffer, and other conditions were as follows.

Template amount (genomic DNA): 5 ng
Primer concentration: 0.1 to 0.2 µM
Total reaction mixture volume: 15 µL PCR cycle: (i) 95° C.×2 min., (ii) 95° C.×30 sec., (iii) 50 to 60° C.×30 sec., (iv) 72° C.×1 min., (v) (ii) to (iv) steps× 35 to 45 cycles, and (vi) kept at 15° C.

The PCR products were treated with restriction enzymes, subjected to electrophoresis using 4% agarose gel to analyze cleaved product fragment lengths for typing.

(7) Genotyping

Genotype was determined based on the fluorescence intensities of two colors detected as a result of the invader assay reaction described in (5) above. 463 SNPs on 33 genes were thus typed for the genotypes of patients by invader assay. Further, 26 SNPs on 13 genes were similarly typed for genotypes by PCR-RFLP described in (6) above.

(8) Result 1 (SNPs Investigating Research Useful for Identifying CR+PR Groups and PD Group)

In 86 accumulated cases, 3 cases were evaluated as non-responsive, 8 cases had no metastatic focus, and 24 cases had invariable response evaluation (NC group=No Change group) (including one case with no metastatic focus). Excluding these 34 cases, the remaining 52 cases were used for analysis. They were CR group (Complete Response group), PR group (Partial Response group), and PD group (Progressive Disease group). The evaluation of these treatment responses were in accordance with General Rules for Renal Carcinoma, April, 1999, 3$^{rd}$ edition. The rules can be further referred to in the followings: "Guidelines to Evaluate the response to Chemotherapy in Solid Tumors" (*J. Jpn. Soc. Cancer Ther.*, 21 (5): 929-924, June, 1986), published by Japan Society of Clinical Oncology.

For all 463 SNPs to be analyzed as to whether or not they can be identification factors for these cases, identification ability of each SNP was examined by a statistical discriminant analysis. SNPs with a level of significance being p>0.1 in terms of Pearson's chi-square test were presumed to have low identification ability, and hence excluded from the analysis.

Thus, 445 SNPs were excluded from 463 SNPs, leaving 18 SNPs as candidates. Further, when there are a plurality of variables strongly correlated with each other, only one variable among those needs to be examined for identification ability due to the characteristics of multivariate analysis. For this reason, SNPs strongly correlated with each other were investigated using Cramer's V statistic (L. D. Fisher and G. V. Belle, *Biostatistics, A Methodology for the Health Sciences,*

278, 1993, John Wiley & Sons, Inc., New York) before performing logistic regression analysis, narrowing down the numbers of SNPs to be analyzed from 18 to 16.

The final SNPs left as a result of the above analysis were assumed to have identification ability after adjusting influences by background factors relating to tumor suppression, using a stepwise logistic regression model (L. D. Fisher and G. V. Belle, *Biostatistics, A Methodology for the Health Sciences*, 638-647, 1993, John Wiley & Sons, Inc., New York).

The background factors adjusted were sex, age, histlogical findings (cell type, grade, pT, pM, incipience and recurrence, lung metastasis, liver metastasis, brain metastasis, bone metastasis, limph node metastasis). The level of significance used was 0.05.

The results are shown in Table 3 and Table 4.

TABLE 3

|  |  | Total | NC + PD Groups | | CR + PR Groups | | $X^2$ test |
|---|---|---|---|---|---|---|---|
|  |  |  | N | % | N | % | P value |
| STAT1-18 | AA | 73 | 46 | 63.01 | 27 | 36.99 | 0.0710 |
|  | AG | 2 | 0 | 0.00 | 2 | 100.00 |  |
|  | Total | 75 | 46 | 61.33 | 29 | 38.67 |  |
| STAT3-2 | CC | 22 | 18 | 81.82 | 4 | 18.18 | 0.0094 |
|  | CT | 42 | 25 | 59.52 | 17 | 40.48 |  |
|  | TT | 11 | 3 | 27.27 | 8 | 72.73 |  |
|  | Total | 75 | 46 | 61.33 | 29 | 38.67 |  |
| STAT3-3 | GG | 25 | 21 | 84.00 | 4 | 16.00 | 0.0033 |
|  | GC | 47 | 30 | 63.83 | 17 | 36.17 |  |
|  | CC | 11 | 3 | 27.27 | 8 | 72.73 |  |
|  | Total | 83 | 54 | 65.06 | 29 | 34.94 |  |
| STAT3-18 | CT | 9 | 3 | 33.33 | 6 | 66.67 | 0.0660 |
|  | TT | 66 | 43 | 65.15 | 23 | 34.85 |  |
|  | Total | 75 | 46 | 61.33 | 29 | 38.67 |  |
| STAT3-21 | AA | 12 | 4 | 33.33 | 8 | 66.67 | 0.0184 |
|  | AG | 41 | 24 | 58.54 | 17 | 41.46 |  |
|  | GG | 22 | 18 | 81.82 | 4 | 18.18 |  |
|  | Total | 75 | 46 | 61.33 | 29 | 38.67 |  |
| STAT3-25 | CC | 12 | 4 | 33.33 | 8 | 66.67 | 0.0184 |
|  | CT | 41 | 24 | 58.54 | 17 | 41.46 |  |
|  | TT | 22 | 18 | 81.82 | 4 | 18.18 |  |
|  | Total | 75 | 46 | 61.33 | 29 | 38.67 |  |
| STAT3-31 | CT | 10 | 3 | 30.00 | 7 | 70.00 | 0.0288 |
|  | TT | 65 | 43 | 66.15 | 22 | 33.85 |  |
|  | Total | 75 | 46 | 61.33 | 29 | 38.67 |  |
| STAT3-52 | AA | 12 | 4 | 33.33 | 8 | 66.67 | 0.0184 |
|  | AC | 41 | 24 | 58.54 | 17 | 41.46 |  |
|  | CC | 22 | 18 | 81.82 | 4 | 18.18 |  |
|  | Total | 75 | 46 | 61.33 | 29 | 38.67 |  |
| STAT3-17 | CC | 8 | 7 | 87.50 | 1 | 12.50 | 0.0346 |
|  | CG | 36 | 25 | 69.44 | 11 | 30.56 |  |
|  | GG | 31 | 14 | 45.16 | 17 | 54.84 |  |
|  | Total | 75 | 46 | 61.33 | 29 | 38.67 |  |
| SSI3-1 | AA | 52 | 37 | 71.15 | 15 | 28.85 | 0.0183 |
|  | AC | 20 | 7 | 35.00 | 13 | 65.00 |  |
|  | CC | 3 | 2 | 66.67 | 1 | 33.33 |  |
|  | Total | 75 | 46 | 61.33 | 29 | 38.67 |  |

TABLE 4

|  |  | Total | NC + PD Groups | | CR + PR Groups | | $X^2$ test |
|---|---|---|---|---|---|---|---|
|  |  |  | N | % | N | % | P value |
| IL4R-14 | AC | 9 | 8 | 88.89 | 1 | 11.11 | 0.0704 |
|  | CC | 66 | 38 | 57.58 | 28 | 42.42 |  |
|  | Total | 75 | 46 | 61.33 | 29 | 38.67 |  |
| IL4R-29 | CT | 17 | 14 | 82.35 | 3 | 17.65 | 0.0430 |
|  | TT | 58 | 32 | 55.17 | 26 | 44.83 |  |
|  | Total | 75 | 46 | 61.33 | 29 | 38.67 |  |
| IL4R-22 | AA | 61 | 34 | 55.74 | 27 | 44.26 | 0.0378 |
|  | AC | 14 | 12 | 85.71 | 2 | 14.29 |  |
|  | Total | 75 | 46 | 61.33 | 29 | 38.67 |  |
| IRF2-82 | CC | 11 | 4 | 36.36 | 7 | 63.64 | 0.0572 |
|  | CT | 23 | 7 | 30.43 | 16 | 69.57 |  |
|  | TT | 18 | 12 | 66.67 | 6 | 33.33 |  |
|  | Total | 52 | 23 | 44.23 | 29 | 55.77 |  |
| IRF2-67 | AA | 6 | 1 | 16.67 | 5 | 83.33 | 0.0547 |
|  | AC | 31 | 20 | 64.52 | 11 | 35.48 |  |
|  | CC | 37 | 25 | 67.57 | 12 | 32.43 |  |
|  | Total | 74 | 46 | 62.16 | 28 | 37.84 |  |
| ICSBP-38 | AA | 36 | 20 | 55.56 | 16 | 44.44 | 0.0833 |
|  | AC | 32 | 19 | 59.38 | 13 | 40.63 |  |
|  | CC | 7 | 7 | 100.00 | 0 | 0.00 |  |
|  | Total | 75 | 46 | 61.33 | 29 | 38.67 |  |
| PTGS1-3 | CC | 70 | 45 | 64.29 | 25 | 35.71 | 0.0495 |
|  | CT | 5 | 1 | 20.00 | 4 | 80.00 |  |
|  | Total | 75 | 46 | 61.33 | 29 | 38.67 |  |
| PTGS1-4 | CT | 7 | 1 | 14.29 | 6 | 85.71 | 0.0073 |
|  | TT | 68 | 45 | 66.18 | 23 | 33.82 |  |
|  | Total | 75 | 46 | 61.33 | 29 | 38.67 |  |
| PTGS1-5 | AG | 9 | 2 | 22.22 | 7 | 77.78 | 0.0102 |
|  | GG | 66 | 44 | 66.67 | 22 | 33.33 |  |
|  | Total | 75 | 46 | 61.33 | 29 | 38.67 |  |
| PTGS2-12 | AG | 9 | 8 | 88.89 | 1 | 11.11 | 0.0704 |
|  | GG | 66 | 38 | 57.58 | 28 | 42.42 |  |
|  | Total | 75 | 46 | 61.33 | 29 | 38.67 |  |
| TAP2-5 | AA | 3 | 3 | 100.00 | 0 | 0.00 | 0.0717 |
|  | AG | 18 | 14 | 77.78 | 4 | 22.22 |  |
|  | GG | 54 | 29 | 53.70 | 25 | 46.30 |  |
|  | Total | 75 | 46 | 61.33 | 29 | 38.67 |  |

Since the only background factor determined as being good for evaluating by logistic regression analysis was the presence/absence of lung metastasis, it was forcibly incorporated into a model, whereby the stepwise logistic regression analysis was adopted to analyze 13 SNPs. The results are shown in Table 5.

TABLE 5

| | Step 0. Lung metastasis entered | | | Step 1. Lung metastasis & IL4R-29 combined | | |
|---|---|---|---|---|---|---|
| Effect | DF | Chi-Square | Pr > ChiSq | Effect | DF | Chi-Square | Pr > ChiSq |
| | Wald | | | | Wald | | |
| Lung metastasis | 1 | 5.7899 | 0.0161 | Lung metastasis | 1 | 5.0697 | 0.0243 |
| | | | | IL4R-29 | 1 | 5.0220 | 0.0250 |

TABLE 5-continued

| | | Step 0. Lung metastasis entered | | | Step 1. Lung metastasis & IL4R-29 combined | | |
|---|---|---|---|---|---|---|---|
| Effect | DF | Chi-Square | Pr > ChiSq | Effect | DF | Chi-Square | Pr > ChiSq |
| | | Score | | | | Score | |
| STAT3-2 | 2 | 7.3400 | 0.0255 | STAT3-2 | 2 | 6.2350 | 0.0443 |
| IL4R-14 | 1 | 1.9023 | 0.1678 | IL4R-14 | 1 | 0.0069 | 0.9337 |
| IL4R-29 | 1 | 5.6613 | 0.0173 | | | | |
| IL4R-22 | 1 | 5.3691 | 0.0205 | IL4R-22 | 1 | 1.7277 | 0.1887 |
| IRF2-67 | 2 | 3.1816 | 0.2038 | IRF2-67 | 2 | 3.4973 | 0.1740 |
| IRF2-82 | 2 | 6.4242 | 0.0403 | IRF2-82 | 2 | 7.2690 | 0.0264 |
| PTGS1-4 | 1 | 1.6800 | 0.1949 | PTGS1-4 | 1 | 1.4449 | 0.2294 |
| PTGS1-5 | 1 | 2.3196 | 0.1278 | PTGS1-5 | 1 | 2.9970 | 0.0834 |
| TAP2-5 | 2 | 7.6356 | 0.0220 | TAP2-5 | 2 | 9.7880 | 0.0075 |

In Table 5, the items under "Effect" are the SNPs that were tested. "DF" means Degree of Freedom.

Wald Chi-square means Wald's Chi-square statistical test, and Score chi-square means Score's chi-square ($\chi^2$) statistical test, Pr>ChiSq is P value of Wald's chi-square test or Score's chi-square test.

As shown in Table 5, Step 0 indicates the identification abilities of the SNPs after adjusting influence by the presence of lung metastasis. SNPs with P value smaller than 0.05 are indicated as useful for identification even after adjusting influence by the presence of lung metastasis.

The results revealed that the SNPs found useful for identification are STAT3-2, IL-4R-29, IL-4r-22, IRF2-82, and TAP2-5. IL-4R-29, that was indicated as having the highest identification ability among these six SNPs, was incorporated into the logistic regression analysis model (lung metastasis adjustment).

P values in Step 1 of Table 5 show the identification abilities of the remaining SNPs when lung metastasis presence/absence and IL-4R-29 were combined. The SNPs with P values smaller than 0.05 were suggested to have independent identification information from IL-4R-29. Such SNPs were STAT3-2, IRF2-82, and TAP2-5. The combination of IL-4R-29 and TAP2-5 were suggested to have the highest identification ability after adjusting the influence by presence/absence of lung metastasis. When combined with IL-4R-29 in this step, no SNPs became newly significant.

In conclusion of the results shown in Table 5, SNPs, that are suggested as being identification markers for patients with renal cell cancers with expected tumor suppression of primary focus and metastatic focus, are STAT3-2, IRF2-82, IL-4R-22, and TAP2-5 which became significant in Step 0, in addition to IL-4R-29, the best candidate.

The incorporation of this stage classification into the model prevented decline of statistical detection caused by non-uniform background factors of patients, adjusted such non-uniform background factors of patients between two groups, and confirmed significance value differences between the two groups.

Example 2

SNPs Investigating Research Useful for Identifying CR+PR Groups and NC+PD Groups Using the samples from the subjects described in EXAMPLE 1, cases wherein the NC group was added to the PD group were analyzed for given gene polymorphisms relating to IFN therapeutic effects on renal cell cancers.

Reasons for the unchanging size of tumors in the NC group were presumed to be that tumors did not respond to IFN, or tumors responded to IFN but grew too big in size and their appearance showed no change. The IFN response evaluation depended on which reason was taken, but in this example the NC group was considered non-responsive group due to the invariable size of tumors. Based on this consideration, the NC group was added to the PD group as described above to perform gene polymorphism typing.

Out of 86 collected cases, 3 cases were evaluated as non-responsive, while 8 cases had no metastasis focus. These 11 cases were removed, leaving 75 cases for analysis.

In the same manner as in Example 1, the individual identification abilities of 463 SNPs were analyzed by a statistical discriminant analysis, and SNPs presumed to have low identification ability were excluded from analysis candidates. As a result of this screening, 441 SNPs were excluded from 463 SNPs, leaving 23 SNPs as candidates.

Further, combinations of SNPs that strongly correlated with each other were investigated using Cramer's V before performing logistic regression analysis, narrowing down the numbers of SNPs to be analyzed from 23 to 17.

The final 17 SNPs were evaluated for identification abilities using the stepwise logistic regression model after adjusting the influence by background factors relevant to tumor suppression.

The background factor adjusted was lung metastasis only, which was found possibly related to tumor suppression in Example 1 above. The level of significance was 0.05. Tables 6 and 7 show the analysis results of 23 SNPs with a level of significance of $p \leq 0.1$ as individual SNP identification ability.

TABLE 6

| | | | NC + PD groups | | CR + PR groups | | $X^2$ test |
|---|---|---|---|---|---|---|---|
| | | Total | N | % | N | % | P value |
| STAT1-18 | AA | 73 | 46 | 63.01 | 27 | 36.99 | 0.0710 |
| | AG | 2 | 0 | 0.00 | 2 | 100.00 | |
| | Total | 75 | 46 | 61.33 | 29 | 38.67 | |
| STAT3-2 | CC | 22 | 18 | 81.82 | 4 | 18.18 | 0.0094 |
| | CT | 42 | 25 | 59.52 | 17 | 40.48 | |
| | TT | 11 | 3 | 27.27 | 8 | 72.73 | |
| | Total | 75 | 46 | 61.33 | 29 | 38.67 | |
| STAT3-18 | CT | 9 | 3 | 33.33 | 6 | 66.67 | 0.0660 |
| | TT | 66 | 43 | 65.15 | 23 | 34.85 | |
| | Total | 75 | 46 | 61.33 | 29 | 38.67 | |
| STAT3-21 | AA | 12 | 4 | 33.33 | 8 | 66.67 | 0.0184 |
| | AG | 41 | 24 | 58.54 | 17 | 41.46 | |
| | GG | 22 | 18 | 81.82 | 4 | 18.18 | |
| | Total | 75 | 46 | 61.33 | 29 | 38.67 | |
| STAT3-25 | CC | 12 | 4 | 33.33 | 8 | 66.67 | 0.0184 |
| | CT | 41 | 24 | 58.54 | 17 | 41.46 | |
| | TT | 22 | 18 | 81.82 | 4 | 18.18 | |
| | Total | 75 | 46 | 61.33 | 29 | 38.67 | |
| STAT3-31 | CT | 10 | 3 | 30.00 | 7 | 70.00 | 0.0288 |
| | TT | 65 | 43 | 66.15 | 22 | 33.85 | |
| | Total | 75 | 46 | 61.33 | 29 | 38.67 | |
| STAT3-52 | AA | 12 | 4 | 33.33 | 8 | 66.67 | 0.0184 |
| | AC | 41 | 24 | 58.54 | 17 | 41.46 | |
| | CC | 22 | 18 | 81.82 | 4 | 18.18 | |
| | Total | 75 | 46 | 61.33 | 29 | 38.67 | |
| STAT3-17 | CC | 8 | 7 | 87.50 | 1 | 12.50 | 0.0346 |

TABLE 6-continued

|  |  |  | NC + PD groups | | CR + PR groups | | $X^2$ test |
|---|---|---|---|---|---|---|---|
|  |  | Total | N | % | N | % | P value |
|  | CG | 36 | 25 | 69.44 | 11 | 30.56 |  |
|  | GG | 31 | 14 | 45.16 | 17 | 54.84 |  |
|  | Total | 75 | 46 | 61.33 | 29 | 38.67 |  |
| SSI3-1 | AA | 52 | 37 | 71.15 | 15 | 28.85 | 0.0183 |
|  | AC | 20 | 7 | 35.00 | 13 | 65.00 |  |
|  | CC | 3 | 2 | 66.67 | 1 | 33.33 |  |
|  | Total | 75 | 46 | 61.33 | 29 | 38.67 |  |
| IL4R-14 | AC | 9 | 8 | 88.89 | 1 | 11.11 | 0.0704 |
|  | CC | 66 | 38 | 57.58 | 28 | 42.42 |  |
|  | Total | 75 | 46 | 61.33 | 29 | 38.67 |  |

TABLE 7

|  |  |  | NC + PD groups | | CR + PR groups | | $X^2$ test |
|---|---|---|---|---|---|---|---|
|  |  | Total | N | % | N | % | P value |
| IL4R-29 | CT | 17 | 14 | 82.35 | 3 | 17.65 | 0.0430 |
|  | TT | 58 | 32 | 55.17 | 26 | 44.83 |  |
|  | Total | 75 | 46 | 61.33 | 29 | 38.67 |  |
| IL4R-22 | AA | 61 | 34 | 55.74 | 27 | 44.26 | 0.0378 |
|  | AC | 14 | 12 | 85.71 | 2 | 14.29 |  |
|  | Total | 75 | 46 | 61.33 | 29 | 38.67 |  |
| IRF2-8 | CC | 41 | 26 | 63.41 | 15 | 36.59 | 0.0601 |
|  | CG | 28 | 19 | 67.86 | 9 | 32.14 |  |
|  | GG | 6 | 1 | 16.67 | 5 | 83.33 |  |
|  | Total | 75 | 46 | 61.33 | 29 | 38.67 |  |
| IRF2-67 | AA | 6 | 1 | 16.67 | 5 | 83.33 | 0.0547 |
|  | AC | 31 | 20 | 64.52 | 11 | 35.48 |  |
|  | CC | 37 | 25 | 67.57 | 12 | 32.43 |  |
|  | Total | 74 | 46 | 62.16 | 28 | 37.84 |  |
| ICSBP-38 | AA | 36 | 20 | 55.56 | 16 | 44.44 | 0.0833 |
|  | AC | 32 | 19 | 59.38 | 13 | 40.63 |  |
|  | CC | 7 | 7 | 100.00 | 0 | 0.00 |  |
|  | Total | 75 | 46 | 61.33 | 29 | 38.67 |  |

TABLE 7-continued

|  |  |  | NC + PD groups | | CR + PR groups | | $X^2$ test |
|---|---|---|---|---|---|---|---|
|  |  | Total | N | % | N | % | P value |
| PTGS1-3 | CC | 70 | 45 | 64.29 | 25 | 35.71 | 0.0495 |
|  | CT | 5 | 1 | 20.00 | 4 | 80.00 |  |
|  | Total | 75 | 46 | 61.33 | 29 | 38.67 |  |
| PTGS1-4 | CT | 7 | 1 | 14.29 | 6 | 85.71 | 0.0073 |
|  | TT | 68 | 45 | 66.18 | 23 | 33.82 |  |
|  | Total | 75 | 46 | 61.33 | 29 | 38.67 |  |
| PTGS1-5 | AG | 9 | 2 | 22.22 | 7 | 77.78 | 0.0102 |
|  | GG | 66 | 44 | 66.67 | 22 | 33.33 |  |
|  | Total | 75 | 46 | 61.33 | 29 | 38.67 |  |
| PTGS2-12 | AG | 9 | 8 | 88.89 | 1 | 11.11 | 0.0704 |
|  | GG | 66 | 38 | 57.58 | 28 | 42.42 |  |
|  | Total | 75 | 46 | 61.33 | 29 | 38.67 |  |
| TAP2-5 | AA | 3 | 3 | 100.00 | 0 | 0.00 | 0.0717 |
|  | AG | 18 | 14 | 77.78 | 4 | 22.22 |  |
|  | GG | 54 | 29 | 53.70 | 25 | 46.30 |  |
|  | Total | 75 | 46 | 61.33 | 29 | 38.67 |  |

Cramer's V values, denoting the degree of correlation among the 23 SNPs, were obtained, and the results revealed that the identification abilities of STAT3-2, STAT3-21, STAT3-25, and STAT3-52 were considered approximately identical. Similarly, the identification abilities of STAT3-18 and STAT3-31 were equal, and those of IL-4R-14, IL-4R-18, and IL-4R-26 were also equal. Consequently, STATA3-2, STAT3-18, and IL-4R-14 were used in a multivariate analysis as representatives from each group. As a result, 17 SNPs were left for analysis.

Out of 75 cases in which the presence or absence of lung metastasis were verified, 2 cases with partially missing SNP analysis data were excluded, leaving 73 cases as final candidates for analysis.

The presence or absence of lung metastasis was forcibly entered to the model, and 17 SNPs were subjected to stepwise logistic regression analysis. The results were shown in Table 8 below in the same manner as in Table 5 above.

TABLE 8

| | Step 0. Lung metastasis incorporated | | | Step 1. Lung metastasis Combined with STAT3-2 | | | Step 2 Lung metastasis combined with STAT-3-2 and PTGS1-4 | | |
|---|---|---|---|---|---|---|---|---|---|
| Effect | DF | Chi-Square | Pr > ChiSq | Effect | DF | Chi-Square | Pr > ChiSq | Effect | DF | Chi-Square | Pr > ChiSq |
| Wald | | | | Wald | | | | Wald | | | |
| Lung metastasis | 1 | 3.8108 | 0.0509 | Lung metastasis | 1 | 5.1389 | 0.0234 | Lung metastasis | 1 | 4.3194 | 0.0377 |
|  |  |  |  | STAT3-2 | 2 | 8.5747 | 0.0137 | STAT3-2 | 2 | 9.5303 | 0.0085 |
|  |  |  |  |  |  |  |  | PTGS1-4 | 1 | 5.8760 | 0.0153 |
| Score | | | | Score | | | | Score | | | |
| STAT3-2 | 2 | 10.1494 | 0.0063 |  |  |  |  |  |  |  |  |
| STAT3-18 | 1 | 2.3568 | 0.1247 | STAT3-18 | 1 | 0.8408 | 0.3592 | STAT3-18 | 1 | 1.3914 | 0.2382 |
| STAT3-17 | 2 | 7.3217 | 0.0257 | STAT3-17 | 2 | 2.5509 | 0.2793 | STAT3-17 | 2 | 4.0085 | 0.1348 |
| SSI3-1 | 2 | 8.6995 | 0.0129 | SSI3-1 | 2 | 8.0291 | 0.0181 | SSI3-1 | 2 | 5.1540 | 0.0760 |
| IL4R-14 | 1 | 2.1852 | 0.1393 | IL4R-14 | 1 | 1.3708 | 0.2417 | IL4R-14 | 1 | 2.2697 | 0.1319 |
| IL4R-29 | 1 | 3.0538 | 0.0806 | IL4R-29 | 1 | 1.4259 | 0.2324 | IL4R-29 | 1 | 1.0758 | 0.2996 |
| IL4R-22 | 1 | 5.5655 | 0.0183 | IL4R-22 | 1 | 4.3939 | 0.0361 | IL4R-22 | 1 | 4.9985 | 0.0254 |
| IRF2-82 | 2 | 3.1171 | 0.2104 | IRF2-82 | 2 | 2.7241 | 0.2561 | IRF2-82 | 2 | 4.9090 | 0.0859 |
| IRF2-67 | 2 | 4.7653 | 0.0923 | IRF2-67 | 2 | 4.5890 | 0.1008 | IRF2-67 | 2 | 6.7774 | 0.0338 |
| ICSBP-38 | 2 | 4.4645 | 0.1073 | ICSBP-38 | 2 | 8.7789 | 0.0124 | ICSBP-38 | 2 | 8.8930 | 0.0117 |

TABLE 8-continued

| | Step 0. Lung metastasis incorporated | | | Step 1. Lung metastasis Combined with STAT3-2 | | | Step 2 Lung metastasis combined with STAT-3-2 and PTGS1-4 | | | |
|---|---|---|---|---|---|---|---|---|---|---|
| Effect | DF | Chi-Square | Pr > ChiSq | Effect | DF | Chi-Square | Pr > ChiSq | Effect | DF | Chi-Square | Pr > ChiSq |
| PTGS1-3 | 1 | 3.1113 | 0.0778 | PTGS1-3 | 1 | 3.8519 | 0.0497 | PTGS1-3 | 1 | 0.6413 | 0.4232 |
| PTGS1-4 | 1 | 6.0039 | 0.0143 | PTGS1-4 | 1 | 8.3082 | 0.0039 | | | | |
| PTGS1-5 | 1 | 5.3353 | 0.0209 | PTGS1-5 | 1 | 6.5818 | 0.0103 | PTGS1-5 | 1 | 0.8721 | 0.3504 |
| PTGS2-12 | 1 | 3.5120 | 0.0609 | PTGS2-12 | 1 | 4.5064 | 0.0338 | PTGS2-12 | 1 | 3.4298 | 0.0640 |
| TAP2-5 | 2 | 5.8287 | 0.0542 | TAP2-5 | 2 | 7.1057 | 0.0286 | TAP2-5 | 2 | 5.2362 | 0.0729 |

Step 0 in Table 8 shows the identification abilities of SNPs after adjusting influence by the presence or absence of lung metastasis. The SNPs with P values smaller than 0.05 were indicated as being good for identification even after adjusting influence by the presence/absence of lung metastasis. The SNPs found to be good for identification were STAT3-2, STAT3-17, SSI3-1, IL-4R-22, PTGS1-4, and PTGS1-5. STAT3-2, which showed the highest identification ability among these 6 SNPs, was incorporated into the model.

P values in Step 1 indicate the identification abilities of each of remaining SNPs when the presence or absence of lung metastasis was combined with STAT3-2. The SNPs with P values smaller than 0.05 were suggested to have independent identification information from STAT3-2. Such SNPs were SSI3-1, IL-4R-22, ICSBP-38, PTGS1-3, PTGS1-4, PTGS1-5, PTGS2-12, and TAP2-5. Among these, the combination of STAT3-2 and PTGS1-4 was suggested to have the highest identification ability after adjusting influence by the presence or absence of lung metastasis. SNPs suggested as being useful for the first time when combined with STAT3-2 were ICSBP-38, PTGS1-3, PTGS2-12, and TAP2-5.

Step 2 shows the identification abilities of each of the remaining SNPs when the presence/absence of lung metastasis was combined with STAT3-2 and PTGS1-4. Variables suggested as having independent information from STAT3-2 and PTGS1-4 and being useful when combined with them were IL-4R-22, IRF2-67, and ICSBP-38. IRF2-67 was suggested as being a useful SNP for identification for the first time at this stage.

In conclusion of the results shown in Table 8, SNPs suggested as being identification markers for patients with renal cell cancers with expected tumor suppression of primary focus and metastasis focus are, in addition to STAT3-2, the best candidate, STAT3-17, SSI3-1, IL-4R-22, PTGS1-4, and PTGS1-5 which became significant in Step 0; ICSBP-38, PTGS1-3, PTGS2-12, and TAP2-5 which became newly significant in Step 1; and IRF2-67 which became newly significant in Step 2.

The analysis results in Examples 1 and 2 revealed that STAT3-2, IL-4R-29, IL-4R-14, IL-4R-22, IRF2-82, and TAP2-5 were gene polymorphisms relevant to IFN therapeutic effect (tumore suppression effect) on renal cell cancer in the comparison between CR+PR groups and the PD group, and that TAP2-5, STAT3-17, SSI3-1, IL-4R-22, PTGS1-4, PTGS1-5, ICSBP-38, PTGS1-3, PTGS2-12, TAP2-5, and IRF2-67 were also considered as such in the comparison between CR+PR groups and NC+PD groups.

In the comparison between CR+PR groups and the PD group, STAT3-2 was indicated as having the highest identification ability, and in the comparison between CR+PR groups and NC+PD groups, IL-4R-29 was indicated as having the highest identification ability.

Under a separate experiment, STAT3-3 was found to be equally associated with STAT3-18.

According to the results obtained above, the present invention can thus provide a method for predicting interferon therapy response of a patient with renal cell cancer by preparing, as gene polymorphisms relevant to IFN therapeutic efficacy (tumor-suppression effect) on renal cell cancer, a genomic sequence or a complementary strand thereof from a specimen of the patient with renal cell cancer, determining the genomic DNA sequence or a complementary DNA sequence thereof, using as an identification marker for the presence of a gene polymorphism or genotype of at least one gene selected from the group consisting of STAT3-2, STAT3-3, STAT3-17, STAT3-18, SSI3-1, IL-4R-22, IRF2-67, IRF2-82, ICSBP-38, PTGS1-3, PTGS1-4, PTGS1-5, PTGS2-12, TAP2-5, IL-4R-14, IL-4R-29, and IRF2-67

INDUSTRIAL APPLICABILITY

According to the present invention, the presence of a gene polymorphism relevant to IFN therapy effect (tumor-suppression effect) on renal cell cancer is detected, whereby the detected polymorphism, as an indication, can be advantageously used as an identification marker responsive to IFN therapy for renal cell cancer.

SEQUENCE LISTING FREE TEXT

Sequence Numbers: 1-32 show primer sequences.

The invention claimed is:

1. A method for evaluating responsiveness of renal cell cancer in a human patient to natural IFN-alpha and recombinant IFN-alpha therapy, comprising the steps of: (i) obtaining a DNA sample derived from a human with renal cell cancer, (ii) analyzing said DNA sample to determine the genotype at position 4243095 of the STAT3 gene, and (iii) identifying the renal cell cancer of the human as being responsive to interferon alpha therapy when the genotype at position 4243095 of the STAT3 gene is C/T or T/T.

2. The method for evaluating responsiveness of renal cell cancer in a human patient to interferon therapy of claim 1, wherein the genotype at position 4243095 of the STAT3 gene is determined by at least one method selected from the group consisting of: direct sequencing; allele specific oligonucleotide (ASO)-dot blot analysis; single nucleotide primer extension; PCR-single-strand conformation polymorphism (SSCP) analysis; PCR-restriction fragment length polymorphism (RFLP) analysis; invader assay; quantitative realtime PCR; and mass array using a mass spectrometer.

3. The method of claim 2, wherein the genotype at position 4243095 of the STAT3 gene is determined by invader assay or direct sequencing.

4. The method of claim 2, wherein the genotype at position 4243095 of the STAT3 gene is determined by PCR-RFLP analysis.

5. The method according to claim 2, wherein the genotype at position 4243095 of the STAT3 gene is determined using an oligonucleotide having a sequence consisting of at least 10 consecutive bases containing a gene polymorphism site with genotype C/T or T/T at position 4243095 of the STAT3 gene.

6. A method according to claim 2, wherein the gene polymorphism detection primer is a pair of oligonucleotide primers consisting of SEQ ID Nos. 1 and 17.

7. The method according to claim 1, further comprising analyzing said DNA sample to determine the genotype at one or more positions selected from the group consisting of (i) position 4264926 of STAT3 gene, (ii) position 4204027 of STAT3 gene, (iii) position 4050541 of STAT3(KCNH4) gene, (iv) position 10246541 of SSI3 gene, (v) position 18686025 of IL-4R gene, (vi) position 17736877 of IRF2 gene, (vii) position 17744613 of IRF2 gene, (viii) position 390141 of ICSBP gene, (ix) position 26793813 of PTGS1 gene, (x) position 26794182 of PTGS1 gene, (xi) position 2679019 of PTGS1 gene, (xii) position 15697329 of PTGS2 gene, (xiii) position 23602539 of TAP2 gene, (xiv) position 18686068 of IL-4R gene, and (xv) position 1868553 of IL-4R gene.

8. The method of claim 7, wherein the genotype at each of the position of (i) to (xv) is determined by a gene polymorphism detection primer pair as follows:

the gene polymorphism detection primer pair of (i) is SEQ ID Nos. 2 and 18, the gene polymorphism detection primer pair of (ii) is SEQ ID Nos. 3 and 19, the gene polymorphism detection primer pair of (iii) is SEQ ID Nos. 4 and 20, the gene polymorphism detection primer pair of (iv) is SEQ ID Nos. 5 and 21, the gene polymorphism detection primer pair of (v) is SEQ ID Nos. 6 and 22, the gene polymorphism detection, primer pair of (vi) is SEQ ID Nos. 7 and 23, the gene polymorphism detection primer pair of (vii) is SEQ ID Nos. 8 and 24, the gene polymorphism detection primer pair of (viii) is SEQ ID Nos. 9 and 25, the gene polymorphism detection primer pair of (ix) is SEQ ID Nos. 10 and 26, the gene polymorphism detection primer pair of (x) is SEQ ID Nos. 11 and 27, the gene polymorphism detection primer pair of (xi) is SEQ ID Nos. 12 and 28, the gene polymorphism detection primer pair of (xii) is SEQ ID Nos. 13 and 29, the gene polymorphism detection primer pair of (xiii) is SEQ ID Nos. 14 and 30, the gene polymorphism detection primer pair of (xiv) is SEQ ID Nos. 15 and 31, and the gene polymorphism detection primer pair of (xv) is SEQ ID Nos. 16 and 32.

* * * * *

UNITED STATES PATENT AND TRADEMARK OFFICE
CERTIFICATE OF CORRECTION

| | |
|---|---|
| PATENT NO. | : 7,838,229 B2 |
| APPLICATION NO. | : 11/666056 |
| DATED | : November 23, 2010 |
| INVENTOR(S) | : Toyokazu Seki et al. |

It is certified that error appears in the above-identified patent and that said Letters Patent is hereby corrected as shown below:

Column 43, Line 22: Delete "2679019" and insert -- 26794619 --, therefor

Signed and Sealed this
Second Day of October, 2012

David J. Kappos
*Director of the United States Patent and Trademark Office*

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial
<220> FEATURE:
```

<223> OTHER INFORMATION: Primer sequence (forward) for STAT3-2

<400> SEQUENCE: 1
gagagtggga ggagggagag                                                  20

<210> SEQ ID NO 2
<211> LENGTH: 20
<212> TYPE: DNA
<213> ORGANISM: Artificial
<220> FEATURE:
<223> OTHER INFORMATION: Primer sequence (forward) for STAT3-3

<400> SEQUENCE: 2
gcagccagtg gaagaatagg                                                  20

<210> SEQ ID NO 3
<211> LENGTH: 20
<212> TYPE: DNA
<213> ORGANISM: Artificial
<220> FEATURE:
<223> OTHER INFORMATION: Primer sequence (forward) for STAT3-17

<400> SEQUENCE: 3
ggcctgaagt gacttttttgg                                                 20

<210> SEQ ID NO 4
<211> LENGTH: 20
<212> TYPE: DNA
<213> ORGANISM: Artificial
<220> FEATURE:
<223> OTHER INFORMATION: Primer sequence (forward) for STAT3-18

<400> SEQUENCE: 4
gttacaaggc tgaaggctgc                                                  20

<210> SEQ ID NO 5
<211> LENGTH: 20
<212> TYPE: DNA
<213> ORGANISM: Artificial
<220> FEATURE:
<223> OTHER INFORMATION: Primer sequence (forward) for SSI3-1

<400> SEQUENCE: 5
tccacttgtg gttgctatcg                                                  20

<210> SEQ ID NO 6
<211> LENGTH: 20
<212> TYPE: DNA
<213> ORGANISM: Artificial
<220> FEATURE:
<223> OTHER INFORMATION: Primer sequence (forward) for IL-4R-22

<400> SEQUENCE: 6
tgcaagtcag gttgtctgga                                                  20

<210> SEQ ID NO 7
<211> LENGTH: 20
<212> TYPE: DNA
<213> ORGANISM: Artificial
<220> FEATURE:
<223> OTHER INFORMATION: Primer sequence (forward) for IRF2-67

<400> SEQUENCE: 7
actgatgaac cggtttgctt                                                  20

```
<210> SEQ ID NO 8
<211> LENGTH: 20
<212> TYPE: DNA
<213> ORGANISM: Artificial
<220> FEATURE:
<223> OTHER INFORMATION: Primer sequence (forward) for IRF2-82

<400> SEQUENCE: 8
tgaagaaaag gggtgtggag                                              20

<210> SEQ ID NO 9
<211> LENGTH: 20
<212> TYPE: DNA
<213> ORGANISM: Artificial
<220> FEATURE:
<223> OTHER INFORMATION: Primer sequence (forward) for ICSBP-38

<400> SEQUENCE: 9
ggtttgtgat tacggctggt                                              20

<210> SEQ ID NO 10
<211> LENGTH: 20
<212> TYPE: DNA
<213> ORGANISM: Artificial
<220> FEATURE:
<223> OTHER INFORMATION: Primer sequence (forward) for PTGS1-3

<400> SEQUENCE: 10
tccaggactg agcgtgacta                                              20

<210> SEQ ID NO 11
<211> LENGTH: 20
<212> TYPE: DNA
<213> ORGANISM: Artificial
<220> FEATURE:
<223> OTHER INFORMATION: Primer sequence (forward) for PTGS1-4

<400> SEQUENCE: 11
atcccatgaa gggggtttag                                              20

<210> SEQ ID NO 12
<211> LENGTH: 20
<212> TYPE: DNA
<213> ORGANISM: Artificial
<220> FEATURE:
<223> OTHER INFORMATION: Primer sequence (forward) for PTGS1-5

<400> SEQUENCE: 12
gaagggatgg aaagggagag                                              20

<210> SEQ ID NO 13
<211> LENGTH: 20
<212> TYPE: DNA
<213> ORGANISM: Artificial
<220> FEATURE:
<223> OTHER INFORMATION: Primer sequence (forward) for PTGS2-12

<400> SEQUENCE: 13
tcagacagca aagcctaccc                                              20

<210> SEQ ID NO 14
<211> LENGTH: 20
<212> TYPE: DNA
<213> ORGANISM: Artificial
<220> FEATURE:
<223> OTHER INFORMATION: Primer sequence (forward) for TAP2-5
```

```
<400> SEQUENCE: 14
gggtaggagg taggaggcag                                              20

<210> SEQ ID NO 15
<211> LENGTH: 20
<212> TYPE: DNA
<213> ORGANISM: Artificial
<220> FEATURE:
<223> OTHER INFORMATION: Primer sequence (forward) for IL-4R-14

<400> SEQUENCE: 15
ctctctggga cacggtgact                                              20

<210> SEQ ID NO 16
<211> LENGTH: 20
<212> TYPE: DNA
<213> ORGANISM: Artificial
<220> FEATURE:
<223> OTHER INFORMATION: Primer sequence (forward) for IL-4R-29

<400> SEQUENCE: 16
tgtcctctac cttttccccc                                              20

<210> SEQ ID NO 17
<211> LENGTH: 21
<212> TYPE: DNA
<213> ORGANISM: Artificial
<220> FEATURE:
<223> OTHER INFORMATION: Primer sequence (reverse) for STAT3-2

<400> SEQUENCE: 17
tcccaaagtg acaggttttt g                                            21

<210> SEQ ID NO 18
<211> LENGTH: 20
<212> TYPE: DNA
<213> ORGANISM: Artificial
<220> FEATURE:
<223> OTHER INFORMATION: Primer sequence (reverse) for STAT3-3

<400> SEQUENCE: 18
cacatggttc cccagatacc                                              20

<210> SEQ ID NO 19
<211> LENGTH: 20
<212> TYPE: DNA
<213> ORGANISM: Artificial
<220> FEATURE:
<223> OTHER INFORMATION: Primer sequence (reverse) for STAT3-17

<400> SEQUENCE: 19
aggcttcctt ttgttccgtt                                              20

<210> SEQ ID NO 20
<211> LENGTH: 20
<212> TYPE: DNA
<213> ORGANISM: Artificial
<220> FEATURE:
<223> OTHER INFORMATION: Primer sequence (reverse) for STAT3-18

<400> SEQUENCE: 20
accgtcccct acaatgtctg                                              20

<210> SEQ ID NO 21
<211> LENGTH: 20
```

```
<212> TYPE: DNA
<213> ORGANISM: Artificial
<220> FEATURE:
<223> OTHER INFORMATION: Primer sequence (reverse) for SSI3-1

<400> SEQUENCE: 21
attacatcta ctccggggc                                           20

<210> SEQ ID NO 22
<211> LENGTH: 20
<212> TYPE: DNA
<213> ORGANISM: Artificial
<220> FEATURE:
<223> OTHER INFORMATION: Primer sequence (reverse) for IL-4R-22

<400> SEQUENCE: 22
tgcgatgtgt ggagttgttt                                          20

<210> SEQ ID NO 23
<211> LENGTH: 20
<212> TYPE: DNA
<213> ORGANISM: Artificial
<220> FEATURE:
<223> OTHER INFORMATION: Primer sequence (reverse) for IRF2-67

<400> SEQUENCE: 23
gtagcctcca tctgtgccat                                          20

<210> SEQ ID NO 24
<211> LENGTH: 20
<212> TYPE: DNA
<213> ORGANISM: Artificial
<220> FEATURE:
<223> OTHER INFORMATION: Primer sequence (reverse) for IRF2-82

<400> SEQUENCE: 24
gtcaatgttt ggcggagttc                                          20

<210> SEQ ID NO 25
<211> LENGTH: 20
<212> TYPE: DNA
<213> ORGANISM: Artificial
<220> FEATURE:
<223> OTHER INFORMATION: Primer sequence (reverse) for ICSBP-38

<400> SEQUENCE: 25
ttgggaaagg cacagaattt                                          20

<210> SEQ ID NO 26
<211> LENGTH: 20
<212> TYPE: DNA
<213> ORGANISM: Artificial
<220> FEATURE:
<223> OTHER INFORMATION: Primer sequence (reverse) for PTGS1-3

<400> SEQUENCE: 26
ggacttgact cagtgcccat                                          20

<210> SEQ ID NO 27
<211> LENGTH: 20
<212> TYPE: DNA
<213> ORGANISM: Artificial
<220> FEATURE:
<223> OTHER INFORMATION: Primer sequence (reverse) for PTGS1-4

<400> SEQUENCE: 27
```

```
aatcttgcag cctgacacct                                               20

<210> SEQ ID NO 28
<211> LENGTH: 20
<212> TYPE: DNA
<213> ORGANISM: Artificial
<220> FEATURE:
<223> OTHER INFORMATION: Primer sequence (reverse) for PTGS1-5

<400> SEQUENCE: 28
ggagggactc acccaagaat                                               20

<210> SEQ ID NO 29
<211> LENGTH: 20
<212> TYPE: DNA
<213> ORGANISM: Artificial
<220> FEATURE:
<223> OTHER INFORMATION: Primer sequence (reverse) for PTGS2-12

<400> SEQUENCE: 29
tgggagcagg aaagaactga                                               20

<210> SEQ ID NO 30
<211> LENGTH: 21
<212> TYPE: DNA
<213> ORGANISM: Artificial
<220> FEATURE:
<223> OTHER INFORMATION: Primer sequence (reverse) for TAP2-5

<400> SEQUENCE: 30
ttttcatgcc tctttcaggt g                                             21

<210> SEQ ID NO 31
<211> LENGTH: 20
<212> TYPE: DNA
<213> ORGANISM: Artificial
<220> FEATURE:
<223> OTHER INFORMATION: Primer sequence (reverse) for IL-4R-14

<400> SEQUENCE: 31
gtggagtgtg aggaggagga                                               20

<210> SEQ ID NO 32
<211> LENGTH: 20
<212> TYPE: DNA
<213> ORGANISM: Artificial
<220> FEATURE:
<223> OTHER INFORMATION: Primer sequence (reverse) for IL-4R-29

<400> SEQUENCE: 32
agtagaaccc gagatgccct                                               20
```